United States Patent [19]

Nomura et al.

[11] Patent Number: 5,081,245

[45] Date of Patent: Jan. 14, 1992

[54] CARBOXYLIC ACID DERIVATIVES

[75] Inventors: Hiroaki Nomura, Osaka; Hiroshi Akimoto, Hyogo; Eiko Imamiya, Osaka; Keizo Inoue, Tokyo, all of Japan

[73] Assignee: Takeda Chemical Industries, Ltd., Osaka, Japan

[21] Appl. No.: 395,524

[22] Filed: Aug. 18, 1989

[30] Foreign Application Priority Data

Aug. 19, 1988 [JP] Japan .................... 63-206969
Mar. 30, 1989 [JP] Japan .................... 1-80593

[51] Int. Cl.⁵ .............. C07D 207/36; C07D 233/70;
C07D 237/04; C07D 239/34; C07D 241/18;
C07D 251/30; C07D 249/04; C07D 249/12;
C07D 253/07; C07D 257/08; C07D 261/12;
C07D 263/36; C07D 265/28; C07D 271/04;
C07D 277/34; C07D 277/68; C07D 279/12;
C07D 285/02; C07D 401/12; C07D 403/12;
C07D 413/12; C07D 417/12; C07D 237/28;
C07D 237/32

[52] U.S. Cl. .................... 544/316; 548/530;
548/531; 548/536; 548/412; 548/413; 548/518;
548/519; 548/532; 548/533; 548/534; 548/535;
548/537; 548/538; 548/541; 548/542; 548/543;
548/544; 548/550; 548/551; 548/336; 548/317;
548/318; 548/319; 548/320; 548/321; 548/337;
548/374; 548/375; 548/376; 548/377; 548/111;
548/112; 548/225; 548/226; 548/227; 548/228;
548/229; 548/230; 548/232; 548/216; 548/243;
548/244; 548/181; 548/117; 548/147; 548/182;
548/183; 548/184; 548/125; 548/119;
548/263.2; 548/263.4; 548/255; 548/118;
548/263.8; 548/264.2; 548/264.4; 548/251;
548/127; 548/130; 548/129; 548/136; 548/138;
548/139; 548/140; 548/141; 548/142; 548/221;
548/217; 548/113; 548/219; 548/159; 548/157;
548/161; 548/163; 548/169; 548/170; 548/171;
548/557; 548/567; 548/569; 548/572; 548/565;
548/348; 548/351; 548/352; 548/353; 548/341;
548/342; 548/379; 548/378; 548/236; 548/187;
548/204; 548/215; 548/156; 548/166; 548/180;
548/507; 548/512; 548/414; 548/415; 548/471;
548/465; 548/466; 548/467; 548/468; 548/472;
548/473; 548/478; 548/479; 548/483; 548/484;
548/485; 548/486; 548/490; 548/491; 548/410;
548/359; 548/371; 548/372; 548/950; 548/573;
548/248; 546/187; 546/188; 546/192; 546/193;
546/189; 546/190; 546/191; 546/200; 546/201;
546/208; 546/209; 546/210; 546/211; 546/215;
546/216; 546/219; 546/220; 546/221; 546/222;
546/21; 546/23; 546/24; 546/25; 546/22;
546/256; 546/261; 546/269; 546/270; 546/271;
546/272; 546/273; 546/275; 546/276; 546/277;
546/278; 546/279; 546/296; 546/297; 546/298;
546/300; 546/301; 546/302; 546/16; 546/242;
546/241; 546/341; 546/342; 546/47; 546/72;
546/74; 546/78; 546/53; 546/155; 546/156;
546/157; 546/140; 546/141; 546/142; 546/138;
546/122; 546/123; 546/238; 546/248; 546/226;
544/337; 544/383; 544/384; 544/385; 544/359;
544/360; 544/361; 544/362; 544/363; 544/364;
544/365; 544/366; 544/367; 544/368; 544/369;
544/370; 544/371; 544/372; 544/373; 544/382;
544/80; 544/82; 544/83; 544/84; 544/85;
544/86; 544/87; 544/113; 544/116; 544/119;
544/120; 544/121; 544/122; 544/123; 544/124;
544/127; 544/128; 544/129; 544/130; 544/131;
544/132; 544/133; 544/134; 544/135; 544/137;
544/138; 544/139; 544/140; 544/141; 544/143;
544/144; 544/157; 544/158; 544/159; 544/160;
544/161; 544/162; 544/163; 544/164; 544/168;
544/169; 544/170; 544/171; 544/172; 544/173;
544/174; 544/175; 544/176; 544/177; 544/70;
544/57; 544/58.1; 544/58.2; 544/58.4;
544/58.5; 544/58.6; 544/58.7; 544/60; 544/232;
544/238; 544/239; 544/240; 544/241; 544/230;
544/243; 544/295; 544/296; 544/300; 544/301;
544/302; 544/310; 544/311; 544/312; 544/313;
544/314; 544/317; 544/318; 544/319; 544/320;
544/321; 544/357; 544/405; 544/406; 544/407;
544/408; 544/219; 544/214; 544/335

[58] Field of Search .............. 544/316, 337, 383, 384,
544/385, 359, 360, 361, 362, 363, 364, 365, 366,
367, 368; 544/369, 370, 371, 372, 373, 382, 80,
82, 83, 84, 85, 86, 87, 113, 116; 544/119, 120,
121, 122, 123, 124, 127, 128, 129, 130, 131, 132,
133, 134, 135; 544/137, 138, 139, 140, 141, 143,
144, 157, 158, 159, 160, 161, 162, 163, 164;
544/168, 169, 170, 171, 172, 173, 174, 175, 176,
177, 70, 57, 58.1, 58.2, 58.4; 544/58.5, 58.6,
58.7, 60, 232, 238, 239, 240, 241, 230, 243, 295,
296, 300, 301; 544/302, 310, 311, 312, 313, 314,
317, 318, 319, 320, 321, 357, 405, 406, 407;
544/408, 219, 214, 335, 333, 224, 399, 264, 276,
277, 244, 265, 266, 267, 268; 544/269, 270, 271,
272, 235, 231, 237, 354, 283, 284, 285, 286, 287,
288, 289; 544/290, 291, 292, 293, 257, 258, 259,
260; 540/597, 596, 598, 599, 600, 601, 602, 603,
604, 553, 575, 542; 548/530, 531, 536, 412, 413,
518, 519, 532, 533, 534, 535, 537, 538, 541, 542;
548/543, 544, 550, 551, 336, 317, 318, 319, 320,
321, 337, 374, 375, 376, 377; 548/111, 112, 225,
226, 227, 228, 229, 230, 232, 216,
548/243, 244, 181, 117, 147; 548/182, 183, 184,
125, 119, 255, 118, 263.8, 263.4, 263.2, 127, 251,
264.2, 264.4, 130; 548/129, 136, 138, 139, 140,
141, 142, 221, 217, 113, 219, 159, 157, 161, 163;
548/169, 170, 171, 557, 567, 569, 572, 565, 348,
351, 352, 353, 341, 342, 379; 548/378, 236, 187,
204, 215, 156, 166, 180, 507, 512, 414, 415, 471,
465, 466; 548/467, 468, 472, 473, 478, 479, 483,
484, 485, 486, 490, 491, 410, 359, 371; 548/372,
950, 573, 248; 546/187, 188, 192, 193, 189, 190,
191, 200, 201, 208, 209, 210, 211, 215, 216;
546/219, 220, 221, 222, 21, 23, 24, 25, 22, 256, (Abstract on next page.)

261, 269, 270, 271, 272; 546/273, 275, 276, 277, 278, 279, 296, 297, 298, 300, 301, 302, 16, 242, 241; 546/341, 342, 147, 172, 174, 18, 153, 155, 156, 157, 140, 141, 142, 138, 122; 546/123, 238, 248, 226

[56] References Cited

U.S. PATENT DOCUMENTS

4,737,518  4/1988  Nomura et al. ............... 514/476

FOREIGN PATENT DOCUMENTS

| | | |
|---|---|---|
| 0094586 | 11/1983 | European Pat. Off. |
| 0109255 | 5/1984 | European Pat. Off. |
| 0142333 | 5/1985 | European Pat. Off. |
| 0238202 | 9/1987 | European Pat. Off. |
| 0254540 | 1/1988 | European Pat. Off. |

OTHER PUBLICATIONS

Hackh's Chemical Dictionary, 4th Edition, p. 447 (1972), McGraw-Hill Book Company, New York.

*Primary Examiner*—John M. Ford
*Attorney, Agent, or Firm*—Wegner, Cantor, Mueller & Player

[57] ABSTRACT

A compound represented by the formula:

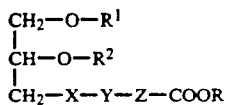

wherein
R represents a hydrogen atom or a lower alkyl group;
$R^1$ represents a higher alkyl group which may be substituted;
$R^2$ represents a hydrogen atom or a lower alkyl group, a lower alkanoyl group or a nitrogen-containing 5- to 7-membered heterocyclic group each of which may be substituted; X represents a divalent group represented by the formula:

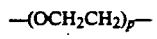

wherein p represents an integer of 1 to 5, a divalent group represented by the formula:

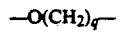

wherein q represents an integer of 3 to 8, or a divalent group represented by the formula:

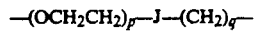

wherein J represents an oxygen atom or a group represented by the formula: $-S(O)_r-$ (wherein r represents 0, 1 or 2), and p and q are the same as defined above; Y represents a divalent group containing tertiary or quaternary nitrogen atom(s); and Z represents an alkylene group which may be substituted and/or interrupted, or a group represented by the formula:

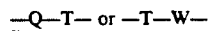

wherein Q and W represent an alkylene group which may be substituted, and T represents a phenylene group, a naphthylene group, a cycloalkylene group; and a salt thereof exhibit excellent antitumor action including differentiation inducing action and are useful as pharmaceuticals.

13 Claims, No Drawings

CARBOXYLIC ACID DERIVATIVES

INDUSTRIAL FIELD OF THE INVENTION

The present invention relates to a carboxylic acid derivative which is useful as a pharmaceutical. More specifically, the present invention provides a compound represented by the following general formula, which is useful as an antitumor agent:

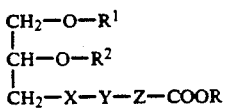

wherein R represents a hydrogen atom or a lower alkyl group; $R^1$ represents a higher alkyl group which may be substituted; $R^2$ represents a hydrogen atom or a lower alkyl group, a lower alkanoyl group or a nitrogen-containing 5- to 7-membered heterocyclic group each of which may be substituted; X represents a divalent group represented by the formula:

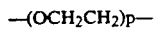

wherein p represents an integer of 1 to 5, a divalent group represented by the formula:

wherein q represents an integer of 3 to 8, or a divalent group represented by the formula:

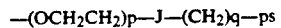

wherein J represents an oxygen atom or a group represented by the formula —S(O)r— (r represents 0, 1 or 2), and p and q are defined as above; Y represents a divalent group containing tertiary or quaternary nitrogen atom(s); Z represents an alkylene group which may be substituted and/or interrupted, or a group represented by the formula:

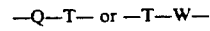

wherein Q and W represent an alkylene group which may be substituted, and T represents a phenylene group, a naphthylene group, a cycloalkylene group,

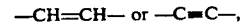

and a salt thereof.

PRIOR ART

With the progress of basic research in biochemistry, differences between cancer cells and normal cells have recently been elucidated step by step. Extraordinary proliferativity, a lack of contact inhibition, and other abnormal features of cancer cells are attributable to structural and functional changes in their cell membranes. Certain kinds of phospholipids, a membrane-acting cell membrane component, are involved in the control of activities of functional proteins in the membrane, having various and significant effects on the function and metabolism of cells and the maintenance of life. In view of these biochemical aspects, there were discovered some compounds having a particular structure factor, among amphipathic glycerolipids, which possess antitumor activities, including a phospholipid represented by formula (II) [W. E. Berdel, W. R. E. Bausert, U. Fink, K. Rostetter and P. G. Munder; Anticancer Research, 1, 345 (1981)]. At present, however, this compound is subject to great limitations in its clinical trial, since it has various adverse effects such as bronchostenosis, platelet aggregation and hypotension due to its structure's similarity to that of platelet activating factor (PAF).

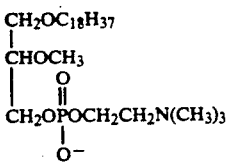

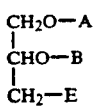

There was also discovered a glycerolipid represented by formula (III) having no phosphate group [A represents a long-chain alkyl; B represents a short- or long-chain alkyl or an acyl having 2 to 5 carbon atoms; E represents —O(CH$_2$)t—G wherein t represents 1 to 12 and G represents an amino group, an acylamino group, a dialkylamino group or a quaternary ammonium group] that possess platelet activating factor (PAF) antagonistic activities and thus have potential for use as a therapeutic drug for PAF-mediated disorders (e.g. anaphylactic shock) [Japanese Patent Unexamined Publication Nos. 100544/1985 and 198445/1983; T. Miyamoto et al., Kyoto Conference of Prostaglandins, Nov. 26-28, 1984, Abst. p. 99]. However, as to glycerolipid (III), improvements in duration of action and therapeutic index are required, and further there is no specific disclosure of antitumor action.

Cancer pharmacotherapy, in comparison with pharmacotherapy for other diseases, has many difficulties in that conventional anticancer agents are poor in selectivity, less effective on solid cancer, and have severe adverse effects and/or high toxicity. Accordingly, concerning cancer treatment, it is now strongly desired that a drug with highly selective toxicity to cancer cells, a drug which is capable of rapidly reaching the cancer tissue and which has low toxicity to the patient, and a drug based on a new action mechanism be developed. With the aim of solving these problems, the present inventors conducted investigations, and developed a means of solving these problems as described below.

DISCLOSURE OF THE INVENTION

In view of these problems, the present inventors considered that an excellent anticancer agent that is less toxic to the host but exhibits highly selective toxicity to cancer cells can exist among amphiphilic lipids having a particular structure factor. It was reported in previous studies that the alkyl ether group-cleaving enzyme activity of cancer cells is usually lower than that of normal cells [R. L. Wykle and F. Snyder, The Enzymes of Biological Membranes, A Martonosi, ed., vol. 2. Plenum Press, New York, 1976, p 87; H. J. Lin, F. C. S. Ho, and C. L. H. Lee, Cancer Res., 38, 946 (1978); M. Modolell, R. Andreesen, W. Pahlke, U. Brugger, and P. C. Munder, Cancer Res., 39, 4681 (1979)].

Therefore, this kind of alkyl ether compound is considered to accumulate at high concentrations in cancer cells, particularly solid cancer lesion tissues, thus having a highly selective antitumor effect and highly selective therapeutic effect. On the other hand, compounds having two functional groups respectively capable of becoming a cation residue and an anion residue in the same molecule, i.e., compounds capable of having a zwitterion structure (e.g. nucleotides, phospholipids, amino acids), exist universally as important functional components of living bodies. It can therefore be thought that amphiphilic zwitterions similar to these biocomponents in structure are widely different from cation type amphiphilic lipids represented by formula (III) in terms of drug effect and/or toxicity.

Taking note of amphiphilic zwitterion compounds obtained by introducing both a tertiary amino group or quaternary ammonium group and a carboxyalkyl group into an ether type derivative of glycerol, the present inventors conducted investigations and found that the compound represented by general formula (I) is less toxic and possesses excellent antitumor activities with highly selective toxicity to various tumor cells. The present inventors conducted further investigations based on this finding, and completed the present invention. Accordingly, the present invention provides the compound represented by above general formula (I) and its salt and their production and use.

In the above general formula (I), the lower alkyl group represented by R includes alkyl groups having 1 to 6 atoms, such as methyl, ethyl, propyl and butyl.

The higher alkyl group represented by $R^1$ includes alkyl groups having 8 to 20 carbon atoms, such as n-decyl, n-undecyl, n-dodecyl, n-tetradecyl, n-hexadecyl, n-octadecyl and n-eicosyl. The higher alkyl group may have substituents, typically one to three, such as a phenyl group, a naphthyl group, a cycloalkyl group, a lower alkyl group, a vinyl group, an acetylene group, a hydroxy group, a lower alkoxy group or a halogen atom. The phenyl group, naphthyl group, cycloalkyl group, vinyl group and ethynyl group may be contained in the form of a divalent group in the higher alkyl group. The methylene moiety, unless it is at the α-position, may be substituted by an oxo group. The cycloalkyl group includes 3- 8-membered cycloalkyl groups, such as cyclopentyl and cyclohexyl. The lower alkyl group includes alkyl groups having 1 to 6 carbon atoms, such as methyl, ethyl, propyl and butyl. The lower alkoxy group includes alkoxy groups having 1 to 6 carbon atoms, such as methoxy, ethoxy, propoxy and butoxy. Examples of the halogen atom as a substituent to the higher alkyl group include fluorine, bromine and chlorine atoms. When $R^1$ is a substituted higher alkyl group, the substitution position may be any one of the substitutable positions in the higher alkyl group. Examples of the substituted higher alkyl group include 12-phenyldodecyl, 12-cyclopentyldodecyl, 10-cyclohexyldecyl, 12-cyclohexyldodecyl, 2-hydroxyoctadecyl, 2-methoxyoctadecyl, 2-oxooctadecyl, 16,16,16-trifluorohexadecyl, 18,18,18-trifluorooctadecyl, 14,14,15,15,16,16,16-heptafluorohexadecyl and 16,16,17,17,18,18,18-heptafluorooctadecyl groups.

The lower alkyl group represented by $R^2$ includes alkyl groups having 1 to 6 carbon atoms, such as methyl, ethyl, propyl, isopropyl, butyl, sec-butyl, tert-butyl, pentyl and hexyl.

The alkanoyl group represented by $R^2$ includes alkanoyl groups having 1 to 6 carbon atoms, such as formyl, acetyl, propionyl, n-butyryl, isobutyryl, pentanoyl, pivaloyl, valeryl and isovaleryl.

Examples of the nitrogen-containing 5- to 7-membered heterocyclic group represented by $R^2$, which may be condensed to form a bicyclic ring, include pyrrolyl, imidazolyl, pyrazolyl, oxazolyl, isooxazolyl, thiazolyl, 1,2,3-oxadiazolyl, triazolyl, tetrazolyl, thiadiazolyl, piperidinyl, N-methylpiperazinyl, N-ethylpiperazinyl, morpholinyl, thiomorpholinyl, pyridyl, pyridazinyl, pyrimidinyl, pyrazinyl, triazinyl, azepinyl, diazepinyl, benzoxazolyl, benzothiazolyl, isoindolyl, indolyl, indolidinyl, indazolyl, purinyl, quinolyl, isoquinolyl, quinolizinyl, phthalazinyl, quinoxalinyl, quinazolinyl, cinnolinyl and pteridinyl groups, and partially or completely hydrogenated groups corresponding to these groups.

The lower alkyl group, lower alkanoyl group or nitrogen-containing 5- to 7-membered heterocyclic group represented by $R^2$ may have 1 to 3 substituents. Examples of the substituent include a halogen atom (e.g. fluorine, bromine, chlorine), a lower ($C_1$-$C_6$) alkyl group (e.g. methyl, ethyl, propyl, butyl, pentyl, hexyl), a lower ($C_2$-$C_6$) alkenyl group (e.g. vinyl, allyl, 1-methylvinyl, 2-methylvinyl), a lower ($C_3$-$C_6$) cycloalkyl group (e.g. cyclopropyl, cyclobutyl, cyclopentyl, cyclohexyl), a lower ($C_5$-$C_6$) cycloalkenyl group (e.g. cyclopentenyl, cyclohexenyl), a phenyl-lower ($C_1$-$C_6$) an alkyl group (e.g. benzyl, α-methylbenzyl, phenethyl), a phenyl group, a lower ($C_1$-$C_6$) alkylthio group, a lower ($C_1$-$C_6$) alkylsulfinyl group, a phenylsulfinyl group, a lower ($C_1$-$C_6$) alkylsulfonyl group, a phenylsulfonyl group, a mercapto group, a sulfino group, a sulfo group, a phosphono group, a sulfamoyl group, an N-lower ($C_1$-$C_6$) alkylsulfamoyl group, an N,N-di-lower ($C_1$-$C_6$) alkylsulfamoyl group (e.g. N,N-dimethylsulfamoyl, N,N-diethylsulfamoyl, N,N-dipropylsulfamoyl, N,N-dibutylsulfamoyl), a 3- to 6-membered cyclic aminosulfonyl group (e.g. 1-pyrrolidinylsulfonyl, 1-piperidinylsulfonyl, 1-piperazinylsulfonyl, 4-methylpiperazin-1-ylsulfonyl, morpholinoosulfonyl), an imino group, an amidino group, an amino group, an N-lower ($C_1$-$C_6$) alkylamino group, an N,N-di-lower ($C_1$-$C_6$) alkylamino group, a 3- to 6-membered cyclic amino group (e.g. 1-azetidinyl, 1-pyrrolidinyl, 1-piperidinyl, 1-piperazinyl, 4-methylpiperazin-1-yl, morpholino), a lower ($C_1$-$C_6$) alkamoyl group, a lower ($C_1$-$C_6$) alkamoyl group, a lower ($C_1$-$C_6$) alkanoylamino group, a benzamido group, a benzoyl group, a lower ($C_1$-$C_6$) alkanoyloxy group, a benzoyloxy group, a lower ($C_1$-$C_6$) alkoxy group, a lower ($C_2$-$C_7$) alkoxycarbonyl group, a phenoxy group, a phenylthio group, a hydroxy group, an oxo group, a thioxo group, an epoxy group, a hydroxy-lower ($C_1$-$C_6$) alkyl group (e.g. hydroxyethyl), an amino-lower ($C_1$-$C_6$) alkyl group, a carboxy group, a carbamoyl group, an N-lower ($C_1$-$C_6$) alkylcarbamoyl group, an N,N-di-lower ($C_1$-$C_6$) alkylcarbamoyl group (e.g. N,N-dimethylcarbamoyl, N,N-diethylcarbamoyl, N,N-dipropylcarbamoyl, N,N-dibutylcarbamoyl), a 3- to 6-membered cyclic aminocarbonyl group (e.g. 1-azetidinylcarbonyl, 1-pyrrolidinylcarbonyl, 1-piperidinylcarbonyl, 1-piperazinylcarbonyl, 4-methylpiperazin-1-ylcarbonyl, morpholinocarbonyl), a cyano group, a trifluoromethyl group and a ureido group.

In formula X, p represents an integer of 1 to 5, preferably 2 or 3; q represents an integer 3 to 8, preferably 4, 5 or 6.

The divalent group represented by Y containing tertiary nitrogen atoms includes a group represented by the formula:

wherein R³ represents a lower alkyl group which may have substituents, and a divalent heterocyclic ring containing tertiary nitrogen atoms which may have substituents.

The divalent group represented by Y containing quaternary nitrogen atoms includes a group represented by the formula:

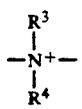

wherein R³ and R⁴ independently represent a lower alkyl group which may have substituents; R³ and R⁴ may, together with the adjacent nitrogen atom, form a cyclic ammonium group, and a divalent heterocyclic ring containing quaternary nitrogen atoms which may have substituents.

The lower alkyl group represented by R³ or R⁴ includes alkyl groups having 1 to 6 carbon atoms (e.g. methyl, ethyl, propyl, butyl, pentyl, hexyl), among which a methyl group is preferred.

Examples of the cyclic ammonium group formed by R³ and R⁴, taken together with the adjacent nitrogen atom, which may be condenses to form a bicyclic ring, include pyrrolinio-1, 1-diyl, pyrrolidinio-1, 1-diyl, imidazolio-1, 1-diyl, imidazolinio-1, 1-diyl, pyrazolio-(1,1) or (2,2)-diyl, piperidinio-1, 1-diyl, piperazinio-1, 1-diyl, morpholinio-4,4-diyl, thiomorpholinio-4,4-diyl, indolinio-1,1-diyl and isoindolinio-2,2-diyl groups.

In the divalent group containing tertiary nitrogen atoms and the divalent group containing quaternary nitrogen atoms represented by Y, R³ or R⁴ may have 1 to 3 substitutable positions. The substituent includes the above-mentioned substituents to the lower alkyl group, lower alkanoyl group or nitrogen-containing 5- to 7-membered heterocyclic group represented by R².

Examples of the divalent heterocyclic group represented by Y containing tertiary nitrogen atoms, which may be condensed to form a bicyclic ring, include pyrrolidine-1,(2 or 3)-diyl, pyrroline-1,(2 or 3)-diyl, pyrrole-1,(2 or 3)-diyl, imidazoline-1,(2,4 or 5)-diyl, imidazole-1,(2,4 or 5)-diyl, pyrazoline-1,(3,4 or 5)-diyl, pyrazole-1,(3,4 or 5)-diyl, oxazole-(2,4 or 5)-diyl, thiazole-(2,4 or 5)-diyl, piperidine-1,(2,3 or 4)-diyl, pyridine-(2,3,4 or 5)-diyl, pyrimidine-(2,4,5 or 6)-diyl, pyridazine-(3,4,5 or 6)-diyl, pyrazine-(2,3,5 or 6)-diyl, piperazine-1,(2 or 3)-diyl, morpholine-(2 or 3),4-diyl, thiomorpholine-(2 or 3),4-diyl, benzoxazole-(2,4,5,6 or 7)-diyl, benzothiazole-(2,4,5,6 or 7)-diyl, isoindole-2,(1,3,4,5,6 or 7)-diyl, indole-1,(2,3,4,5,6 or 7)-diyl, purinediyl, isoquinolinediyl, quinolinediyl, phthalazinediyl, quinoxalinediyl, quinazolinediyl, cinnolinediyl and pteridinediyl groups.

Examples of the divalent heterocyclic group containing quaternary nitrogen atoms represented by Y, which may be condensed to form a bicyclic ring, include 1-[lower (C₁–C₆) alkyl]pyrrolidinio-1,(2 or 3)-diyl, 1-[lower (C₁–C₆) alkyl]-pyrrolinio-1,(2 or 3)-diyl, imidazolio-1,3-diyl, (1 or 3)-mono[lower (C₁–C₆)alkyl]imidazolio-(3 or 1),(2 or 4)-diyl, imidazolinio-1,3-diyl, (1 or 3)-mono[lower (C₁–C₆) alkyl]imidazolinio-(3 or 1),(2 or 4)-diyl, oxazolio-3,(2,4 or 5)-diyl, thiazolio-3,(2,4 or 5)-diyl, pyridinio-1,(2,3 or 4)-diyl, 1-[lower (C₁–C₆) alkyl]piperidinio-1,(2,3 or 4)-diyl, 1-[lower (C₁–C₆) alkyl]piperazinio-1, (2 or 3)-diyl, pyrazinio-1,(2 or 3)-diyl, pyrimidinio-1,(2,4,5 or 6)-diyl, pyridazinio-1,(3 or 4)-diyl, 4-[lower (C₁–C₆) alkyl]morpholinio-4,(2 or 3)-diyl, 4-[lower (C₁–C₆) alkyl]thiomorpholinio-4,(2 or 3)-diyl, benzoxazolio-1,(2,4,5,6 or 7)-diyl, benzothiazolio-1,(2,4,5,6 or 7)-diyl, quinolinio-1,(2,3,4,5,6 or 8)-diyl, isoquinolinio-2,(1,3,4,5,6,7 or 8)-diyl and (1,1 or 1,4)-di[lower (C₁–C₆) alkyl]piperazinio-(4 or 1),(2 or 3)-diyl groups.

These divalent heterocyclic groups represented by Y, containing tertiary nitrogen atoms or quaternary nitrogen atoms, may further have at substitutable positions 1 to 3 substituents exemplified as the abovementioned substituents to the lower alkyl group, lower alkanoyl group or nitrogen-containing 5- to 7-membered heterocyclic group represented by R².

The alkylene group represented by Z includes straight or branched chain alkylene groups having 1 to 13 carbon atoms, such as methylene, ethylene, trimethylene, tetramethylene, pentamethylene, hexamethylene, octamethylene, decamethylene and tridecamethylene, among which straight-chained alkylene groups having 2 to 8 carbon atoms are preferred. The alkylene group may have 1 to 3 substituents exemplified as the abovementioned substituents to the lower alkyl group, lower alkanoyl group or nitrogen-containing 5- to 7-membered heterocyclic group represented by R².

Examples of the alkylene group represented by Z which may be interrupted include the above-mentioned straight or branched chain alkylene group having 1 to 13 carbon atoms, and a group represented by the formula:

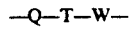

wherein Q and W independently represent a straight or branched chain alkylene group having 1 to 12 carbon atoms; the total number of carbon atoms in Q and W is 2 to 13; and T represents a phenylene group, a naphthylene group, a 3- to 8-membered cycloalkylene group, —CH=CH—, —C≡C—, —NH—, —NH—C(=O)—, —C(=O)—NH—, —O—, —O—C(=O)—, —C(=O)—O—, —S—, —SO— or —SO₂—.

Z may also be a group represented by the formula:

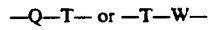

wherein Q and W represent a straight or branched chain alkylene group having 1 to 13 carbon atoms; and T represents a phenylene group, a naphthylene group, 9/3- to 8-membered cycloalkylene group, —CH=CH— or —C≡C—.

The above alkylene groups may have 1 to 3 substituents exemplified as the substituents to the lower alkyl group, lower alkanoyl group or nitrogen-containing 5- to 7-membered heterocyclic group represented by R².

When Y represents a divalent group containing tertiary nitrogen atoms, compound (I) may form a pharmaceutically acceptable salt with an inorganic acid (e.g. hydrochloric acid, hydrobromic acid, hydriodic acid, boric acid, phosphoric acid, nitric acid, sulfuric acid) or an organic acid (e.g. acetic acid, lactic acid, tartaric acid, citric acid, methanesulfonic acid, ethanesulfonic acid, benzenesulfonic acid, toluenesulfonic acid).

When Y represents a divalent group containing quaternary nitrogen atoms, compound (I) may form a salt with an anion (W−). The anion as W− includes pharmaceutically acceptable anions such as an anion of an inorganic acid (e.g. hydrochloric acid, hydrobromic acid, hydriodic acid, boric acid, phosphoric acid, nitric acid, sulfuric acid) or an anion of an organic acid (e.g. acetic acid, lactic acid, tartaric acid, citric acid, methanesulfonic acid, ethanesulfonic acid, benzenesulfonic acid, toluenesulfonic acid).

When Y represents a divalent group containing tertiary nitrogen atoms or a divalent group containing quaternary nitrogen atoms, the compound may form an intramolecular salt with an anion present in the molecule. Examples of the intramolecular anion include a carboxylate group ($COO^-$ group), a phosphate group ($P(O)_2O^-$), a sulfate group ($SO_2O^-$), an oxido group ($O^-$ group) and a sulfido group ($S^-$ group).

Compound (I) has a carboxy group in its molecule. The carboxy group may form a carboxylate or may form a pharmaceutically acceptable salt with alkali metal, alkaline earth metal, nontoxic metal, ammonium, substituted ammonium (e.g. sodium, potassium, lithium, calcium, magnesium, aluminum, zinc, ammonium, trimethylammonium, triethylammonium triethanolammonium, pyridinium, substituted pyridinium), or the like.

R is preferably a hydrogen atom, but may be a lower ($C_1$-$C_6$) alkyl group which can easily be hydrolyzed enzymatically or nonenzymatically to be converted to a hydrogen atoms in vivo.

In the compound of formula (I), the 2-position carbon atom of the glycerol skeleton is an asymmetric center, whose absolute configuration may be any one of S, R or SR (racemic). An asymmetric center may further be present outside the glycerol skeleton; in this case, more than one diastereomer can exist. These diastereomers can easily be separated by ordinary means of separation and purification when necessary. All the diastereomers which can be separated and their mixtures are within the scope of the present invention.

The compound of the present invention can, for example, be produced according to the following reaction schema.

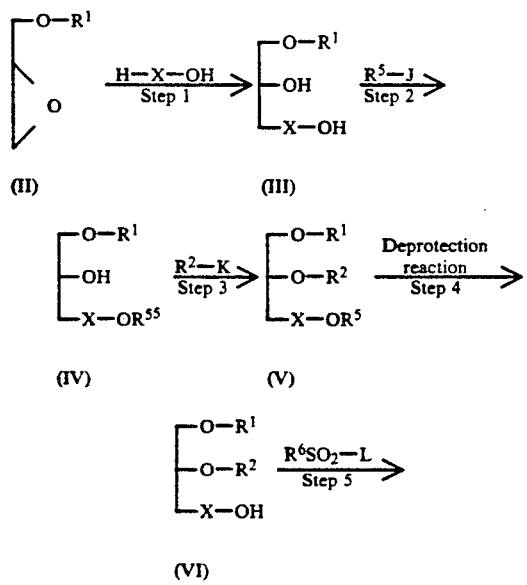

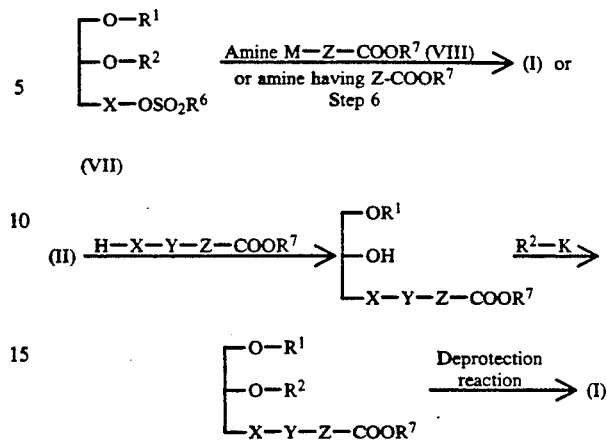

In the above schema, $R^1$, $R^2$, X and Z are the same as defined above; J, K, L and M independently represent an eliminative group, $R^5$ represents a protective group of hydroxyl group; $R^6$ and $R^7$ independently represent a phenyl group, a benzyl group or a lower ($C_{1-6}$) alkyl group each of which may be substituted; $R^7$ may also be a hydrogen atom. Examples of the eliminative group represented by J, K, L and M include a halogen atom (e.g. chlorine, bromine, iodine), a methanesulfonyloxy group, a benzenesulfonyloxy group, a p-toluenesulfonyloxy group, a trifluoromethanesulfonyloxy group and a lower ($C_{1-6}$) alkanoyloxy group.

The phenyl group, benzyl group and lower alkyl group represented by $R^6$ and $R^7$ may be substituted. Examples of the substituent include a lower alkyl group having 1 to 6 carbon atoms (e.g. methyl, ethyl, propyl, isopropyl, butyl, isobutyl, sec-butyl, tert-butyl), a lower alkoxy group having 1 to 6 carbon atoms (e.g. methoxy, ethoxy, propoxy, isopropoxy, n-butoxy, isobutoxy, sec-butoxy, tert-butoxy group), a halogen atom (e.g. fluorine, chlorine, bromine, iodine), a nitro group, a cyano group, a trifluoromethyl group, an N,N-di-lower ($C_1$-$C_6$) alkylamino group (e.g. dimethylamino, diethylamino, dipropylamino, diisopropylamino and dibutylamino group), a lower alkylthio group having 1 to 6 carbon atoms (e.g. methylthio, ethylthio, propylthio, isopropylthio, n-butylthio, sec-butylthio and tert-butylthio group), a lower alkylsulfinyl group having 1 to 6 carbon atoms (e.g. methylsulfinyl, ethylsulfinyl, propylsulfinyl and butylsulfinyl group) and a lower alkylsulfonyl group having 1 to 6 carbon atoms (e.g. methylsulfonyl, ethylsulfonyl, propylsulfonyl and butylsulfonyl group).

The above schema is described in detail below.

Step 1

Glycidyl ether (II) can be produced from alcohol ($R^1OH$) and then reacted with H—X—OH to yield compound (III) by conventional methods.

Step 2

Compound (IV) is derived from compound (III) by protecting the primary hydroxyl group thereof. Examples of protective group $R^5$ include benzyl, p-methoxybenzyl, p-chlorobenzyl, p-nitrobenzyl, t-butyldimethylsilyl, trityl, methoxymethyl, isopropyloxymethyl, tetrahydropyranyl, methyl and t-butyl. The protective group can be introduced in accordance with a known method [J. F. W. McOmie, Protective Groups in Organic Chemistry, Plenum Press, London and New York (1973)].

Step 3

Compound (V) can be produced by reaction of compound (IV) with $R^2$—K in a ratio of 1 to 5 equivalents, preferably 1.5 to 3 equivalents of the latter relative to the former, in an appropriate solvent at $-10°$ to $+80°$ C., preferably $+10°$ to $+40°$ C., in the presence of a base for 1 to 100 hours, preferably 4 to 24 hours. Examples of the base used for the reaction include a metal hydroxide such as sodium hydroxide, potassium hydroxide, lithium hydroxide or barium hydroxide; a metal alkoxide such as sodium methoxide, sodium ethoxide or potassium tert-butoxide; a metal hydride such as sodium hydride or potassium hydride; an organic metal compound such as phenyl lithium or butyl lithium; an aliphatic tertiary amine such as triethylamine; and an aromatic tertiary amine such as pyridine, α-, β- or γ-picoline, 2,6-lutidine, 4-dimethylaminopyridine, 4-(1-pyrrolidinyl)pyridine, dimethylaniline or diethylaniline. Examples of the reaction solvent include water, an alcohol (e.g. tert-butyl alcohol), an ether (e.g. dimethyl ether, diethyl ether, tetrahydrofuran, dioxane, monoglime, diglime), a hydrocarbon halide (e.g. dichloromethane, chloroform, carbon tetrachloride), a nitrile (e.g. acetonitrile), an aliphatic hydrocarbon (e.g. pentane, hexane, heptane, octane), a cycloaliphatic hydrocarbon (e.g. cyclopentane, cyclohexane), an aromatic hydrocarbon (e.g. benzene, toluene, xylene), nitromethane, pyridine, dimethylformamide, dimethyl sulfoxide, hexamethylphosphoramide, sulfolane and an appropriate mixture thereof. The reaction may be carried out in the presence of a phase-transfer catalyst (e.g. cetyltrimethylammonium chloride) in an equivalence ratio of 0.01 to 0.2, preferably 0.02 to 0.5 to 1 of compound (IV), if necessary.

Group ($R^2$) introduced by this step can be chemically converted to another desired group if necessary.

As far as a substituent which is easy to chemically convert are concerned, compound (I) having a desired substituent can be derived by chemically converting only the substituent moiety of compound (I) by a known method. Examples of such conversion of substituents include conversions from a nitro group to an amino group; from an alkanoylamino group to an amino group; from an amino group to a halogen atom, a mono-substituted amino group, a di-substituted amino group or an alkanoylamino group; from a halogen atom to a hydroxyl group, a mercapto group or a cyano group; from a cyano group to a carbamoyl group, an alkoxycarbonyl group or a carboxy group; from a hydroxyl group to a oxo group, an alkoxy group or an alkanoyloxy group; and from an alkoxy group to a hydroxyl group [cf. Pine, Hendrickson, Crum, Hammond; Organic Chemistry (4th ed.) vols. 1 and 2, Hirokawa Shoten (1982)].

Step 4

Compound (VI) can be produced by eliminating the protective group ($R^5$) which is introduced to compound (V) in step 2. The deprotection reaction is carried out in accordance with a known method [J. F. W. McOmie, Protective Groups in Organic Chemistry, Plenum Press, London and New York (1973)], similar to that of step 2.

Step 5

Compound (VII) can be produced by reaction of 1 equivalent of compound (VI) with 0.8 to 1.5 equivalent, preferably 0.85 to 1.05 equivalents, of a reactive derivative of sulfonic acid ($R^6SO_2$—L) in an appropriate anhydrous solvent in the presence of an appropriate basic catalyst or an acid-capture at $-50°$ to $+100°$ C., preferably $-30°$ to $+40°$ C., for 0.5 to 48 hours, preferably 1 to 12 hours. Examples of the anhydrous solvent for the reaction include an ester (e.g. ethyl acetate), an ether (e.g. dimethyl ether, diethyl ether, tetrahydrofuran, dioxane, monoglime, diglime), a hydrocarbon halide (e.g. dichloromethane, chloroform, carbon tetrachloride), a nitrile (e.g. acetonitrile), an aliphatic hydrocarbon (e.g. pentane, hexane, heptane, octane), a cycloaliphatic hydrocarbon (e.g. cyclopentane, cyclohexane), an aromatic hydrocarbon (e.g. benzene, toluene, xylene), nitromethane, pyridine, dimethylformamide, dimethyl sulfoxide, hexamethylphosphoramide, sulfolane and an appropriate mixture thereof. As for the basic catalyst or acid capture there is preferably used a tertiary amine (e.g. an aliphatic tertiary amine such as triethylamine and an aromatic tertiary amine such as pyridine, α-, β- or γ-picoline, 2, 6-lutidine, 4-dimethylaminopyridine, 4-(1-pyrrolidinyl) pyridine, dimethylaniline or diethylaniline).

Step 6

Compound (I) can be produced by reaction of compound (VII) with an excess amount of an amine (primary or secondary amine corresponding to Y) with or without an appropriate solvent at $-20°$ to $+150°$ C., preferably 0° to $+100°$ C., followed by alkylation with a compound represented by formula (VIII):

$$M-Z-COOR^7 \quad \text{(VIII)}$$

wherein M, $R^7$ and Z are the same as defined above. In this step, it is also possible to first alkylate the primary or secondary amine with compound (VIII) and then carry out the reaction with compound (VII). In the case of a secondary or tertiary amine having —Z—COOR$^7$ ($R^7$ and Z are the same as defined above) as a substituent (Y—Z—COOR$^7$), it may be reacted directly with compound (VII). The reaction with the amine can be conducted in a sealed tube at ordinary or increased temperature. The same conditions for the alkylation reaction and the solvent used in step 3 are applicable to this step.

Compound (I) wherein Z represents a group represented by the formula:

$$-Q-T-W-$$

wherein T represents —O—C(=O)—, and Q and W are the same as defined above, can also be produced by (a) a reaction of compound (VII) with a secondary or tertiary amine having —Q—OH as a substituent (Y—Q—OH), followed by an acylation reaction with a compound represented by the formula (VIII'):

$$M'-W-COOR^7 \quad \text{(VIII')}$$

wherein M' represents a carboxyl group or a reactive derivative thereof, and W and $R^7$ are the same as defined above, or (b) acylating the secondary or tertrary amine having —Q—OH as a substituent (Y—Q—OH) with the compound (VIII'), followed by a reaction with the compound (VII). As an example of the means of acylation, there is mentioned a method in which the intermediate represented by the formula:

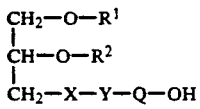

wherein each of the symbols is the same as defined above, which can be obtained by the reaction of compound (VII) with the amine, and the carboxylic acid (VIII') are acylated in the presence of a carbodiimide, diphenylphosphorylazide or diethyl cyanophosphate. Carboxylic acid (VIII') can be used in a molar equivalence ratio of about 1 to 20, preferably 1 to 5, relative to the intermediate. The carbodiimide, diphenylphosphorylazide or diethyl cyanophosphate can be used in a molar equivalence ratio of about 1 to 25, often preferably about 1 to 5, relative to the intermediate. As the carbodiimide, dicyclohexylcarbodiimide is preferred for practical use. Examples of other usable carbodiimides include diphenylcarbodiimide, di-o-tolycarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)-carbodiimide, 1-ethyl-3-(2-diethylaminopropyl)carbodiimide and 1-ethyl-3-(3-diethylaminopropyl)carbodiimide. This acylation reaction may be carried out in the presence of an appropriate solvent. Examples of the solvent include an ester (e.g. ethyl acetate), an ether (e.g. dimethyl ether, diethyl ether, tetrahydrofuran, dioxane, monoglime, diglime), a hydrocarbon halide (e.g. dichloromethane, chloroform, carbon tetrachloride), a nitrile (e.g. acetonitrile), an aromatic hydrocarbon (e.g. benzene, toluene, xylene), nitromethane, pyridine, dimethylformamide, dimethylsulfoxide, hexamethylphosphoramide, sulfolane and an appropriate mixture thereof. This reaction can usually be conducted at a pH value between about 2 and 14, preferably between about 6 and 9, at a temperature between about $-10°$ C. and the boiling point of the solvent (up to about 100° C.), preferably between 0° and 50° C., for about 1 to 100 hours. This acylation reaction can be accelerated by the use of an acylation accelerating catalyst. Such a catalyst includes a basic catalyst and an acidic catalyst. Examples of the basic catalyst include a tertiary amine (e.g. an aliphatic tertiary amine such as triethylamine and an aromatic tertiary amine such as pyridine, $\alpha$-, $\beta$- or $\gamma$-picoline, 2, 6-lutidine, 4-dimethylaminopyridine, 4-(1-pyrrolidinyl) pyridine, dimethylaniline or diethylaniline), an alkali metal halide (e.g. potassium fluoride, anhydrous lithium iodide) and a salt of an organic acid (e.g. sodium acetate). Examples of the acidic catalyst include Lewis acid [e.g. anhydrous zinc chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric chloride, boron trifluoride etherate], an inorganic strong acid (e.g. sulfuric acid, perchloric acid, hydrogen chloride, hydrogen bromide), an organic strong acid (e.g. benzenesulfonic acid, p-toluenesulfonic acid, trifluoroacetic acid, trichloroacetic acid) and an acidic ion exchange resin (e.g. polystyrenesulfonic acid). Among these catalysts, 4-dimethylaminopyridine or 4-(1-pyrrolidinyl)-pyridine is often preferred. The amount of catalyst should be such that acylation is accelerated; it is recommended that the catalyst be used in a molar equivalence ratio of about 0.01 to 10, preferably about 0.1 to 1, relative to the intermediate.

Examples of the reactive derivative of carboxyl group represented by M' include an acid halide (e.g. fluoride, chloride, bromide, iodide), an acid anhydride (e.g. iodoacetic anhydride, isobutyric anhydride, succinic anhydride) and a mixed acid anhydride with a monoalkyl carbonates (e.g. monomethyl carbonate, monoethyl carbonate, monopropyl carbonate, monoisopropyl carbonate, monobutyl carbonate, monoisobutyl carbonate, mono-sec-butyl carbonate, mono-tert-butyl carbonate), an active ester (e.g. cyanomethyl ester, carboethoxymethyl ester, methoxymethyl ester, phenyl ester, o-nitrophenyl ester, p-nitrophenyl ester, p-carbomethoxyphenyl ester, p-cyanophenyl ester, thiophenyl ester), an acid azide, a mixed acid anhydride with a phosphoric acid diester (e.g. dimethyl phosphate, diethyl phosphate, dibenzyl phosphate, diphenyl phosphate), and an acid anhydride with a phosphite diester (e.g. dimethyl phosphite, diethyl phosphite, dibenzyl phosphite, diphenyl phosphite).

When $R^7$ in formula (VIII) is not a hydrogen atom, that is, when the carboxy group is protected by a phenyl group, a benzyl group or a lower ($C_1$-$C_6$) alkyl group, each of which may be substituted, the protective group can easily be eliminated by a known method.

There can also be used another method in which glycidyl ether (II) is condensed with a compound represented by formula (IX):

wherein $R^7$, X, Y and Z are the same as defined above, in place of H—X—OH in step 1, and a group $R^2$ is then introduced under the same conditions as in step 3 and group $R^7$ may be finally eliminated by a known method. This method is especially advantageous when the —X—Y—bond is a carbon—carbon bond. Note that —X—Y—, —X—Y—Z—or —X—Y—Z—$COOR^7$ may be constructed as appropriate during the process of sequential formation of —X—. The reaction conditions for steps 1 to 6 are applicable directly to this reaction.

Even when there is a possibility of influence of a functional group on the reaction in any step, the reaction can be efficiently achieved by conducting appropriate protection/deprotection if necessary.

This protection/deprotection reaction is per se known, and described in detail in the following literature: [J. F. W. McOmie, Protective Groups in Organic Chemistry, Plenum Press, London and New York (1973); M. Fieser and L. Fieser, Reagents for Organic Synthesis, vols. 1-10, Wiley-Interscience, New York, London, Sydney and Toronto (1969-1982)].

A compound of formula (I) wherein Y is a divalent group containing quaternary nitrogen atom(s) can also be produced by reacting a compound of formula (I) wherein Y is a divalent group containing tertiary nitrogen atom(s) with, e.g., a lower ($C_1$-$C_6$) alkyl halide or a lower alkyl ($C_1$-$C_6$) sulfonate. Examples of the lower alkyl sulfonate include a lower ($C_1$-$C_6$) alkyl lower ($C_1$-$C_6$) alkanesulfonate, a lower ($C_1$-$C_6$) alkyl benzenesulfonate and a lower ($C_1$-$C_6$) alkyl lower ($C_1$-$C_6$) alkylbenzenesulfonate. This reaction is usually carried out in a solvent used for step 3 at 0° to $+100°$ C. When Y is a tertiary amino group, a salt of compound (I) may be obtained in the production process for compound (I), but it can also be produced by adding an inorganic or organic acid if necessary. When Y is a divalent group containing quanternary nitrogen atoms, it can be converted to a desired anion using anion exchange resin or other means. It is also possible to produce a salt with carboxylate by adding a base, an alkali or another substance to compound (I) when necessary.

Typical methods of producing compound (I) are described above, but these are not to be construed as limitations of the production method for compound (I).

Compound (I) exhibits improvement and duration of main actions (e.g. antitumor action including differentiation inducing action). Accordingly, it has a life-prolongation effect on cancer-bearing mice inoculated with mouse sarcoma S180 or mouse mammary cancer MM46 cells, and noticeably suppresses the proliferation of human rhinopharyngeal cancer KB cells, human promyelocytic leukemia HL-60 cells, and in addition, human nonparvicellular lung cancer cell lines HUT29 and A549, both known to be highly drug-resistant. Furthermore, compound (I) has no considerably severe adverse effects (platelet aggregation, hypotension or bone marrow toxicity); its administration (intraperitoneal) at a dose of 50 mg/kg body weight is not lethal to mice.

Therefore, compound (I) and its salt can be safely administered as an antitumor agent to a cancer-bearing warm-blooded animal. Method, route and amount of administration can be chosen as appropriate according to the subject animal and symptoms. For a mammal, the dosage is usually 1 to 100 mg/kg body weight, preferably 2 to 50 mg/kg body weight, calculated as compound (I). As for administration frequency, the drug may be administered 1 to 3 times a day or at intervals of 2 to 7 days. Intravenous injection by drip infusion over a long period is also possible to maintain a drug concentration in the tissue of not lower than the minimum required level for a long period. When the drug is administered in combination with serum albumin or a globulin via a parenteral route, further improvement of safety, including prevention of histologic (local) disorders, can be expected without drug effect degradation.

Having excellent hydrophilicity and excellent oleophilicity, compound (I) and its salt can be safely administered orally or parenterally to a mammal directly as powder or after being prepared as a pharmaceutical composition in an appropriate dosage form.

The pharmaceutical composition to be administered contains both an effective amount of compound (I) or its salt and a pharmaceutically acceptable carrier or excipient.

The injectable composition for parenteral administration in accordance with the present invention includes sterile aqueous or nonaqueous solutions, suspensions and emulsions. Examples of the aqueous solutions and suspensions include distilled water for injection and physiological saline. Examples of the nonaqueous solutions and suspensions include intralipid, propylene glycol, polyethylene glycol, a vegetable oil such as olive oil, an alcohol such as ethanol, and polysorbate 80. These compositions may further contain an auxiliary agent such as a preservative, a wetting agent, an emulsifier or a dispersant. The aqueous injection may contain an auxiliary agent such as glucose, serum albumin or serum (plasma) globulin. These compositions are, for example, sterilized by filtration through a bacteria trapping filter, addition of a sterilant, or ultraviolet irradiation. These compositions may also be prepared as sterile solid compositions and then used in solution in sterile water or a sterile solvent for injection. Tablets, capsules and other forms of preparation can also be prepared in accordance with conventional methods. Such a solid composition comprises compound (I) or its salt and at least one inert carrier or excipient such as lactose, mannitol, glucose, hydroxypropylcellulose, microcrystalline cellulose or starch. The composition may be formulated with an additive other than the inert carrier and excipient, e.g. a lubricant such as magnesium stearate and a disintegrator such as fibrin calcium gluconate in accordance with conventional method.

The effects of the present invention are hereinafter described in detail by means of the following test examples.

TEST EXAMPLE 1

Growth Inhibitory Effect ($IC_{50}$) of Compounds Obtained in Examples Against KB Cells Human oral epidermoid carcinoma KB cells ($1 \times 10^4$ cells/ml) were transferred to a 96-well microwell plate at 0.1 ml per well and subjected to stationary culture at 37° C. with 5% $CO_2$ for 24 hours. To the resulting culture was added a 10% MEM (Nissui Junyaku) solution of a compound of an Example, followed by stationary culture at 37° C. with 5% $CO_2$ for 72 hours. The culture broth was then removed using a micropipette. 0.1 ml of a 10% minimal essential medium solution containing 3-(4,5-dimethylthiazol-2-yl)-2,5-diphenyl-2H-tetrazolium bromide (Dojin Kagaku) (1.0 mg/ml) was added, followed by cultivation at 37° C. for 4 hours. 0.1 ml of a 10% sodium dodecylsulfate (Wako Pure Chemical) was then added, followed by cultivation at 37° C. for 24 hours. Optical absorbance at wavelength of 590 nm was determined; the drug concentration at which the cells in the untreated control group had been reduced by 50% was taken as the $IC_{50}$ value of the subject compound. The results obtained are shown in Table 1.

TABLE 1

| Subject compound | $IC_{50}$ (μg/ml) |
| --- | --- |
| Compound of Example 1 | 0.16 |
| Compound of Example 3 | 0.32 |
| Compound of Example 5 | 2.50 |
| Compound of Example 6 | 2.50 |
| Compound of Example 7 | 0.16 |
| Compound of Example 8 | 1.25 |
| Compound of Example 9 | 1.25 |
| Compound of Example 10 | 0.32 |
| Compound of Example 11 | 0.32 |
| Compound of Example 12 | 0.63 |
| Compound of Example 14 | 0.32 |
| Compound of Example 15 | 0.63 |
| Compound of Example 16 | 0.63 |
| Compound of Example 17 | 0.32 |
| Compound of Example 18 | 0.32 |
| Compound of Example 19 | 0.63 |
| Compound of Example 20 | 0.32 |
| Compound of Example 21 | 0.63 |
| Compound of Example 22 | 0.63 |
| Compound of Example 23 | 0.32 |
| Compound of Example 24 | 0.32 |
| Compound of Example 25 | 0.16 |

TEST EXAMPLE 2

Antitumor Activity of Compounds Obtained in Examples on Sarcoma 180 Cells (1) Sarcoma 180 cells were subcutaneously transplanted to the side of the back of ICR mice (5 mice per group) at $1 \times 10^6$ cells per animal. 8, 9, 10, 13, 14, 15, 16, 17 and 20 days after the transplantation (a total of 9 times), the compound of Example 1, dissolved in physiological saline, was orally administered (0.3 mg/mouse). After 21 days, the tumor tissue was excised and weighed. Table 2 shows the tumor growth inhibition ratio, relative to the value obtained in the control group without drug treatment.

TABLE 2

| Subject compound | Growth inhibition ratio (1-T/C %) |
|---|---|
| Compound of Example 1 | 65 |

(2) Sarcoma 180 cells were subcutaneously transplanted to the side of the back of ICR mice (5 mice per group) at $1 \times 10^6$ cells per animal. 8, 9, 12, 13, 15, 16, 19 and 20 days after the transplantation (a total of 8 times), a compound of an Example, dissolved in physiological saline, was intraperitoneally administered (0.1 mg/mouse). After 21 days, the tumor tissue was excised and weighed. Table 3 shows the tumor growth inhibition ratio, relative to the value obtained in the control group without drug treatment.

TABLE 3

| Subject compound | Growth inhibition ratio (1-T/C %) |
|---|---|
| Compound of Example 8 | 66 |
| Compound of Example 12 | 81 |

TEST EXAMPLE 3

Acute Toxicity Test with Compounds of Example in Mice 0.2 ml of a solution of a compound of the Example in physiological saline was intraperitoneally administered once to female CDF-1 mice (5 weeks in age, 5 animals per group). Observation was conducted for 7 days following the administration. Table 4 shows the ratio of the number of mice that died to that of mice that survived.

TABLE 4

| Subject compound | Dosage (mg/kg) | Number of mice that died/number of subject mice |
|---|---|---|
| Compound of Example 1 | 50 | 0/5 |
| Compound of Example 3 | 50 | 0/5 |
| Compound of Example 5 | 50 | 0/5 |
| Compound of Example 6 | 50 | 0/5 |
| Compound of Example 8 | 100 | 0/5 |
| Compound of Example 9 | 100 | 0/5 |
| Compound of Example 10 | 50 | 0/5 |
| Compound of Example 12 | 100 | 0/5 |
| Compound of Example 20 | 100 | 0/5 |
| Compound of Example 21 | 100 | 0/5 |

EXAMPLES

The present invention is hereinafter illustrated in more detail by means of the following reference examples and working examples, but the present invention is not limited to these examples.

REFERENCE EXAMPLE 1

Production of
2-[2-[(2-hydroxy-3-octadecyloxy)propoxy]-ethoxy]ethyl triphenylmethyl ether Epichlorohydrin (74.0 g), stearyl alcohol (54.2 g) and cetyltrimethylammonium chloride (3.2 g) were dissolved in toluene (120 ml). To this solution, a 50% aqueous solution of sodium hydroxide (80 g) was added, followed by stirring at 65° C. for 30 minutes. To this mixture, hexane (80 ml) was added, followed by stirring at 65° C. for 3.5 hours. The reaction mixture was then diluted with hexane (700 ml), followed by filtration to remove the insoluble material. The resulting filtrate was concentrated under reduced pressure to yield crude 1,2-epoxy-3-octadecyloxypropane. The entire amount of this crude product and diethylene glycol (235 g) were dissolved in dioxane (350 ml). To this solution, 60% oily sodium hydride (1.20 g) was added, followed by stirring at room temperature for 30 minutes. The reaction mixture was then heated at 110° C. for 13 hours. After cooling, acetic acid (1.8 g) was added and the dioxane was distilled off under reduced pressure. The resulting residue was dissolved in a mixture of hexane-ether-water. After the organic layer was collected and dried over anhydrous sodium sulfate, the solvent was distilled off under reduced pressure to yield crude 2-[2-[(2-hydroxy-3-octadecyloxy)propoxy]ethoxy]ethanol. This crude product was dissolved in pyridine (300 ml). To this solution, trityl chloride (82 g) was added, followed by stirring at 80° C. for 2 hours. Methanol (10 ml) was then added, followed by stirring under the same conditions as above for 30 minutes. The solvent was distilled off under reduced pressure. The resulting residue was purified by silica gel column chromatography (carrier 1.7 kg; developing solvent, hexane:ethyl acetate=6:1→3:1) to yield the desired compound (80.0 g).

IR (Neat): ν 3420, 2920, 2850, 1490, 1465, 1445, 1110, 1085, 755, 705 cm$^{-1}$. NMR (90 MHz, CDCl$_3$): δ0.87 (3H), 1.23 (32H), 2.60 (1H), 3.17–3.70 (14H), 3.80–4.10 (1H), 7.20–7.60 (15H).

REFERENCE EXAMPLE 2

Production of
2-[2-[3-octadecyloxy-2-(pyrimidin-2-yloxy)-propoxy]ethoxy]ethanol

The compound of Reference Example 1 (11.5 g) was dissolved in tetrahydrofuran (40 ml). To this solution, 2-chloropyrimidine (4.9 g) and 60% oily sodium hydride (1.0 g) were added, followed by stirring at 60° C. for 30 minutes. Methanol (5.0 ml) was then added to decompose the excess portion of the sodium hydride. Most of the solvent was distilled off under reduced pressure. The resulting residue was dissolved in a mixture of hexane-ether-water. After the organic layer was collected and dried over anhydrous sodium sulfate, the solvent was distilled off under reduced pressure to yield crude 2-[2-[3-octadecyloxy-2-(pyrimidin-2-yloxy)-propoxy]ethoxy]ethyl trityl ether. The entire amount of this crude product was dissolved in a mixture of tetrahydrofuran (25 ml) and methanol (15 ml). After addition of concentrated hydrochloric acid (6.0 ml), the mixture was allowed to stand at room temperature for 30 minutes. The reaction mixture was then poured into a 10% potassium carbonate solution (100 ml), followed by distillation of the solvent under reduced pressure. The resulting residue was purified by silica gel column chromatography (carrier, 150 g; developing solvent, hexane:ethyl acetate:acetone=5:1:1→3:1:1) to yield the desired compound (8.0 g).

IR (Neat): ν 3400, 2920, 2855, 1575, 1560, 1465, 1425, 1320, 1115, 1070 cm$^{-1}$. NMR (90 MHz, CDCl$_3$): δ0.87 (3H), 1.27 (32H), 2.63 (1H), 3.40–3.87 (14H), 5.47 (1H), 6.90 (1H), 8.47 (2H).

REFERENCE EXAMPLE 3

Production of
2-[2-[3-octadecyloxy-2-(pyrimidin-2-yloxy)-propoxy]ethoxy]ethyl methanesulfonate The compound of Reference Example 2 (8.0 g) was dissolved in dichloromethane (80 ml). To this solution, triethylamine (2.7 g) was added. Methanesulfonyl chloride (2.5 g) was added dropwise while stirring the mixture at room temperature, followed by stirring for 30 minutes. To the reaction mixture, water (50 ml) was added, followed by stirring for 10 minutes. After adjusting the mixture to pH 3.0 with dilute hydrochloric acid, the organic layer was collected. After the organic layer was washed with water and dried over anhydrous sodium sulfate, the solvent was distilled off under reduced pressure to yield the desired compound (9.2 g).

IR (Nujol): ν 1575, 1565, 1420, 1375, 1340, 1310, 1165, 1115 cm$^{-1}$. NMR (90 MHz, CDCl$_3$): δ0.87 (3H), 1.27 (32H), 3.03 (3H), 3.43 (2H), 3.67–3.87 (10H), 4.33 (3H), 5.50 (1H), 6.97 (1H), 8.57 (2H).

REFERENCE EXAMPLE 4

Production of
1-[2-[2-[3-octadecyloxy-2-(pyrimidin-2-yloxy)-propoxy]ethoxy]ethyl]imidazole The compound of Reference Example 3 (2.95 g) and imidazole (390 mg) were dissolved in tetrahydrofuran (15 ml). To this solution, 60% oily sodium hydride (228 mg) was added while stirring the solution at room temperature. Ten minutes later, dimethyl sulfoxide (10 ml) was added, followed by stirring at 40° C. for 2 hours. The solvent was then distilled off under reduced pressure, and the residue was dissolved in a mixture of hexane-ether-water. After the organic layer collected was dried over anhydrous sodium sulfate, the solvent was distilled off to yield the desired compound (2.85 g).

IR (Neat): ν 2920, 2855, 1575, 1565, 1510, 1465, 1425, 1350, 1320, 1285, 1120, 1105, 1070 cm$^{-1}$. NMR (90 MHz, CDCl$_3$): δ0.87 (3H), 1.27 (32H), 3.37–3.83 (12H), 4.03 (2H), 5.47 (1H), 6.90 (1H), 6.97 (1H), 7.03 (1H), 7.50 (1H), 8.50 (2H).

REFERENCE EXAMPLE 5

Production of
2-[2-[[2-(2,3-epoxypropoxy)-3-octadecyloxy]-propoxy]ethoxy]ethyl triphenylmethyl ether The compound of Reference Example 1 (47.3 ) was dissolved in hexane (100 ml). To this solution, 60% oily sodium hydride (1.9 g) was added, followed by stirring at room temperature for 10 minutes. To this mixture, epibromohydrin (19.2 g) was added dropwise, followed by stirring at room temperature overnight. To the reaction mixture, water (50 ml) was added to decompose the excess portion of the sodium hydride while stirring the mixture, followed by extraction with ether (200 ml). The extract was washed with water and then concentrated to dryness. To the resulting residue, hexane (250 ml) was added, followed by treatment with activated charcoal (2.0 g) and then the mixture was concentrated to dryness to yield the desired compound (50.5 g).

IR (Neat): ν 2930, 2860, 1495, 1465, 1445, 1110, 1090, 1010, 900, 840 cm$^{-1}$. NMR (90 MHz, CDCl$_3$): δ0.87 (3H), 1.27 (32H), 2.50–2.60 (1H), 2.70 (1H), 3.00–3.93 (18H), 7.20–7.50 (15H).

REFERENCE EXAMPLE 6

Production of
2-[2-[[2-(2-hydroxypropoxy)-3-octadecyloxy]-propoxy]ethoxy]ethyl triphenylmethyl ether The compound of Reference Example 5 (50.5 g) was dissolved in ether (200 ml). To this solution, lithium aluminum hydride (1.3 g) was added while stirring the solution on an ice bath, followed by stirring at room temperature for 1 hour. After the excess portion of the lithium aluminum hydride was decomposed with acetone (10 g), water (100 ml) and 50% aqueous sodium hydroxide solution (30 g) were added, and the mixture was allowed to stand overnight. The resulting precipitate was removed by filtration. After the filtrate was diluted with hexane (300 ml), the organic layer was collected, followed by distillation of the solvent under reduced pressure to yield the desired compound (44.6 g).

IR (Neat): ν 3470, 2925, 2860, 1445, 1115, 1090, 705 cm$^{-1}$. NMR (90 MHz, CDCl$_3$): δ0.87 (3H), 1.05 (3H), 1.27 (32H), 3.13–4.00 (18H), 7.17–7.50 (15H).

REFERENCE EXAMPLE 7

Production of
2-[2-[[2-(2-oxopropoxy)-3-octadecyloxy]propoxy]-ethoxy]ethyl triphenylmethyl ether The compound obtained in Reference Example 6 (19.7 g), dissolved in dichloromethane (30 ml), was added dropwise to an oxidizing reagent prepared from oxalyl chloride (2.7 ml) dissolved in dichloromethane (70 ml) and dimethyl sulfoxide (5.1 g) in dichloromethane (15 ml), while stirring at −60° C. Ten minutes later, triethylamine (13.7 g) was added, followed by heating gradually. When the inside temperature of the reaction mixture became 10° C., water (100 ml) and hexane (300 ml) were added to collect the organic layer. The organic layer was washed with dilute hydrochloric acid, an aqueous solution of sodium hydrogen carbonate and then water. After the solvent was distilled off under reduced pressure, the residue was purified by silica gel column chromatography (carrier, 800 g; developing solvent, hexane:ethyl acetate=4:1) to yield the desired compound (17.4 g).

IR (Neat): ν 2925, 2860, 1735, 1720, 1490, 1465, 1445, 1350, 1115, 775, 760, 745, 705 cm$^{-1}$. NMR (90 MHz, CDCl$_3$): δ0.87 (3H), 1.27 (32H), 2.07 (3H), 3.20 (2H), 3.30–3.70 (13H), 4.20 (2H), 7.20–7.50 (15H).

REFERENCE EXAMPLE 8

Production of
2-[2-[[2-(2-oxopropoxy)-3-octadecyloxy]propoxy]-ethoxy]ethanol

The compound obtained in Reference Example 7 (8.1 g) was dissolved in a mixture of tetrahydrofuran (30 ml) and methanol (20 ml). To this solution, concentrated hydrochloric acid (4.0 ml) was added, and this mixture was allowed to stand at room temperature for 100 minutes. After neutralization with an aqueous solution of potassium carbonate, the organic solvent was distilled off under reduced pressure, followed by extraction with hexane-ethyl acetate (1:1, 200 ml). The extract was concentrated to dryness, and the resulting residue was purified by silica gel column chromatography (carrier, 100 g; developing solvent, hexane:ethyl acetate:acetone=6:1:1→3:1:1) to yield the desired compound (4.6 g).

IR (Neat): ν 3400, 2920, 2855, 1730, 1715, 1465, 1350, 1115 cm$^{-1}$. NMR (90 MHz, CDCl$_3$): δ0.87 (3H), 1.27 (32H), 2.13 (3H), 2.50 (2H), 3.33–3.80 (13H), 4.23 (2H).

REFERENCE EXAMPLE 9

Production of 2-[2-[[2-(2-oxopropoxy)-3-octadecyloxy]propoxy]-ethoxy]ethyl methanesulfonate The compound obtained in Reference Example 8 (4.5 g) was methanesulfonylated in the same manner as in Reference Example 3 to yield the desired compound (5.2 g).

IR (Neat): ν 2955, 2855, 1730, 1715, 1465, 1350, 1170, 1110, 1010, 970, 920 cm$^{-1}$. NMR (90 MHz, CDCl$_3$): δ0.87 (3H), 1.27 (32H), 2.17 (3H), 3.03 (3H), 3.33–3.80 (13H), 4.23 (2H), 4.30–4.40 (2H).

REFERENCE EXAMPLE 10

Production of 2-[2-[(2,2-dimethoxypropoxy-3-octadecyloxy)-propoxy]ethoxy]ethyl methanesulfonate The compound obtained in Reference Example 9 (2.5 g) was dissolved in 2,2-dimethoxypropane (50 ml). To this solution, Amberlyst-15 ® (1.5 g) was added, followed by stirring at room temperature for 4 hours. The Amberlyst-15 ® was then removed by filtration. After the filtrate was washed with an aqueous solution of sodium hydrogen carbonate, the solvent was distilled off under reduced pressure. The resulting residue was purified by silica gel column chromatography (carrier, 80 g; developing solvent, hexane:ethyl acetate:acetone=5:1:1) to yield the desired compound (2.2 g).

IR (Neat): ν 2920, 2860, 1465, 1450, 1350, 1175, 1115, 1065, 1040, 920 cm$^{-1}$. NMR (90 MHz, CDCl$_3$): δ0.87 (3H), 1.27 (32H), 1.33 (3H), 3.03 (3H), 3.20 (6H), 3.33–3.80 (15H), 4.30–4.40 (2H).

REFERENCE EXAMPLE 11

Production of 1-[2-[2-[(2,2-dimethoxypropoxy-3-octadecyloxy)-propoxy]ethoxy]ethyl]imidazole The compound obtained in Reference Example 10 (1.43 g), dissolved in tetrahydrofuran (13 ml), was added to a tetrahydrofuran solution (10 ml) of sodium imidazolide as prepared from imidazole (204 mg) and 60% oily sodium hydride (120 mg). The tetrahydrofuran was immediately distilled off. Dimethyl sulfoxide (5.0 ml) was added to the resulting residue, followed by stirring at 50° C. for 1.5 hours. After cooling, water (100 ml) was added, followed by extraction with ether-hexane (1:1, 100 ml). The solvent was then distilled off under reduced pressure to yield the desired compound (1.1 g).

IR (Neat): ν 2930, 2860, 1515, 1465, 1375, 1285, 1250, 1115, 1070, 845 cm$^{-1}$. NMR (90 MHz, CDCl$_3$): δ0.87 (3H), 1.23 (32H), 1.33 (3H), 3.23 (6H), 3.33–3.60 (15H), 3.70 (2H), 4.07 (2H), 6.97 (1H), 7.03 (1H), 7.50 (1H).

REFERENCE EXAMPLE 12

Production of N,N-dimethyl-N-2-[2-[(2,2-dimethoxypropoxy-3-octadecyloxy)propoxy]ethoxy]ethyl]amine The compound obtained in Reference Example 10 (0.97 g) was dissolved in a solution (11 ml) of 20% dimethylamine in toluene. After stirring at room temperature for 17 hours, a solution (5.0 ml) of 20% dimethylamine in toluene was added, and the mixture was allowed to stand at room temperature for 33 hours. The solvent was then distilled off under reduced pressure. The resulting residue was dissolved in hexane (90 ml), washed with water, dried and concentrated to dryness to yield the desired compound (0.85 g).

IR (Neat): ν 2930, 2860, 1465, 1120, 1065, 850 cm$^{-1}$. NMR (90 MHz, CDCl$_3$): δ0.86 (3H), 1.05–1.70 (35H), 2.25 (6H), 2.47 (2H), 3.21 (6H), 3.31–3.75 (15H).

REFERENCE EXAMPLE 13

Production of N,N-dimethyl-N-[2-[2-[3-octadecyloxy-2-(pyrimidin-2-yloxy)propoxy]ethoxy]ethyl]amine The compound obtained in Reference Example 3 (1.20 g) and a solution (14 ml) of 20% dimethylamine in toluene were treated in the same manner as in Reference Example 12 to yield the desired compound (1.10 g).

NMR (90 MHz, CDCl$_3$): δ0.87 (3H), 1.03–1.71 (32H), 2.28 (6H), 2.53 (2H), 3.23–3.85 (12H), 5.47 (1H), 6.88 (1H), 8.47 (2H).

REFERENCE EXAMPLE 14

Production of 4-[(4-tert-butoxycarbonyl)phenyl]butyl methanesulfonate

4-[(4-tert-butoxycarbonyl)phenyl]butyl alcohol (1.00 g) was methanesulfonylated in the same manner as in Reference Example 3 to yield the desired compound (1.32 g).

IR (Neat): ν 1710, 1370, 1350, 1310, 1290, 1170, 1110 cm$^{-1}$. NMR (90 MHz, CDCl$_3$): δ1.60 (9H), 1.67–1.90 (4H), 2.70 (2H), 3.00 (3H), 4.20 (2H), 7.20 (2H), 7.90 (2H).

REFERENCE EXAMPLE 15

Production of 4-[(4-tert-butoxycarbonyl)cyclohexyl]butyl methanesulfonate

4-[(4-tert-butoxycarbonyl)cyclohexyl]butyl alcohol (1.40 g) was methanesulfonylated in the same manner as in Reference Example 3 to yield the desired compound (1.85 g).

IR (Neat): ν 2950, 1725, 1365, 1350, 1170, 1135 cm$^{-1}$. NMR (90 MHz, CDCl$_3$): δ1.13–2.23 (24H), 2.40 (1H), 2.97 (3H), 4.20 (2H).

REFERENCE EXAMPLE 16

Production of 2-[2-[(2-hexyloxy-3-octadecyloxy)propoxy]-ethoxy]ethanol

The procedure of Reference Example 2 was applied for a reaction of the compound of Reference Example 1 (6.75 g) with hexyl bromide (5.0 g) to yield the desired compound (4.09 g).

IR (Neat): ν 3475, 2930, 2860, 1465, 1115, 1065 cm$^{-1}$. NMR (90 MHz, CDCl$_3$): δ0.87 (6H), 1.27 (40H), 2.47 (1H), 3.37–3.83 (17H).

REFERENCE EXAMPLE 17

Production of 2-[2-[(2-hexyloxy-3-octadecyloxy)propoxy]-ethoxy]ethyl methanesulfonate The procedure of Reference Example 3 was applied for a reaction of the compound of Reference Example 16 (4.08 g) and methanesulfonyl chloride (1.40 g) to yield the desired compound (4.70 g).

NMR (90 MHz, CDCl$_3$): δ0.87 (6H), 1.27 (40H), 3.03 (3H), 3.33–3.38 (15H), 4.33–4.43 (2H).

REFERENCE EXAMPLE 18

Production of 2-[2-[2-[3-octadecyloxy-2-(pyrimidin-2-yloxy)-propoxy]ethoxy]ethoxy]ethyl methanesulfonate The synthesis procedures of Reference Examples 1 through 3 were applied, and triethylene glycol was used in place of the diethylene glycol used in Reference Example 1, whereby the desired compound was obtained with an overall yield of 42%.

IR (Neat): ν 2920, 2855, 1575, 1565, 1465, 1420, 1345, 1325, 1170, 1105, 1015 cm$^{-1}$. NMR (90 MHz, CDCl$_3$): δ0.87 (3H), 1.27 (32H), 3.03 (3H), 3.43 (2H), 3.60–3.83 (14H), 4.30–4.43 (2H), 5.47 (1H), 6.90 (1H), 8.47 (2H).

REFERENCE EXAMPLE 19

Production of 4-[3-octadecyloxy-2-(pyrimidin-2-yloxy)propoxy]-butyl methanesulfonate The synthesis procedures of Reference Examples 1 through 3 were applied, and 1,4-butanediol was used in place of diethylene glycol used in Reference Example 1, whereby the desired compound was obtained with an overall yield of 55%.

IR (Nujol): ν 1575, 1565, 1425, 1345, 1330, 1170, 1115, 945 cm$^{-1}$. NMR (90 MHz, CDCl$_3$): δ0.87 (3H), 1.23 (32H), 1.47–1.83 (4H), 2.97 (3H), 3.37–3.80 (8H), 4.20 (2H), 5.43 (1H), 6.90 (1H), 8.47 (2H).

REFERENCE EXAMPLE 20

Production of 2-[2-[3-(12-cyclohexyldodecyloxy)-2-(pyrimidin-2-yloxy)propoxy]ethoxy]ethanol The procedure of Reference Example 2 was applied for a reaction of 2-[2-[3-(12-cyclohexyldodecyloxy)-2-hydroxypropoxy]ethoxy]ethyl triphenylmethyl ether (7.69 g) with 2-chloropyrimidine (3.36 g) to yield the desired compound (4.88 g).

IR (Neat): ν 3425, 2930, 2860, 1580, 1565, 1425, 1330, 1310, 1125, 1065 cm$^{-1}$. NMR (90 MHz, CDCl$_3$): δ1.10–1.80 (33H), 2.63 (1H), 3.39–3.83 (14H), 5.47 (1H), 6.90 (1H), 8.48 (2H).

REFERENCE EXAMPLE 21

Production of 2-[2-[3-(12-cyclohexyldodecyloxy)-2-(pyrimidin-2-yloxy)propoxy]ethoxy]ethyl methanesulfonate The procedure of Reference Example 3 was applied to a reaction of the compound of Reference Example 20 (3.0 g) and methanesulfonyl chloride (1.0 g) to yield the desired compound (3.46 g).

IR (Neat): ν 2950, 2860, 1580, 1565, 1425, 1350, 1175, 1115, 920, 805 cm$^{-1}$. NMR (90 MHz, CDCl$_3$): δ1.00–1.80 (33H), 3.03 (3H), 3.44 (2H), 3.63–3.85 (10H), 4.27–4.38 (2H), 5.44 (1H), 6.90 (1H), 8.48 (2H)

REFERENCE EXAMPLE 22

Production of 3-[3-[2-hydroxy-3-(octadecyloxy)propoxy]propyl]-pyridine

To 3-pyridinepropanol (41.9 g), 60% oily sodium hydride (0.74 g) was added, followed by stirring at room temperature for 15 minutes. Crude 1,2-epoxy-3-octadecyloxypropane (10 g), an intermediate in Reference Example 1, was then added, followed by stirring at room temperature for 67 hours. The excess portion of the 3-pyridinepropanol was distilled off under reduced pressure. After adding a small volume of water to the residue, extraction was conducted with a mixture of hexane and ethyl acetate (1:1, 300 ml). After the extract was washed with water and dried, the solvent was distilled off. The resulting residue was purified by silica gel column chromatography (carrier, 250 g; developing solvent, hexane:ethyl acetate:acetone=4:1:0→3:1:1) to yield the desired compound (5.79 g).

IR (Neat): ν 2930, 2870, 1742, 1480, 1465, 1423, 1238, 1115, 755, 715 cm$^{-1}$. NMR (90 MHz, CDCl$_3$): δ0.86 (3H), 1.25 (32H), 1.77–2.30 (2H), 2.69 (2H), 3.26–3.61 (8H), 3.94–4.20 (1H), 7.11–7.32 (1H), 7.43–7.60 (1H), 8.48 (2H).

REFERENCE EXAMPLE 23

Production of 3-[3-[3-octadecyloxy-2-(pyrimidin-2-yloxy)-propoxy]propyl]pyridine The compound of Reference Example 23 (4.3 g) was dissolved in tetrahydrofuran (50 ml). To this solution, 60% oily sodium hydride (0.37 g) was added, followed by stirring at room temperature for 15 minutes. To this mixture, 2-chloropyrimidine (4.3 g) was added, followed by stirring at 80° C. for 5 hours. The solvent was distilled off and the residue was dissolved in a mixture of dichloromethane-water. The dichloromethane layer was collected and the solvent was distilled off. The resulting residue was purified by silica gel column chromatography (carrier, 100 g; developing solvent, hexane:ethyl acetate:acetone=4:1:0→3:1:1) to yield the desired compound (3.74 g).

IR (Neat): ν 2925, 2860, 1740, 1574, 1558, 1460, 1420, 1328, 1302, 1230, 1112, 1042, 709 cm$^{-1}$. NMR (90 MHz, CDCl$_3$): δ0.87 (3H), 1.03–2.34 (34H), 2.66 (2H), 3.30–3.86 (8H), 5.14–5.67 (1H), 6.93 (1H), 7.08–7.34 (1H), 7.40–7.94 (1H), 8.39–8.66 (4H).

EXAMPLE 1

Production of 6-[3-[2-[2-[3-octadecyloxy-2-(pyrimidin-2-yloxy)-propoxy]ethoxy]ethyl]imidazolio-1yl]hexanoate The compound of Reference Example 4 (0.56 g) and methyl 6-bromohexanoate (0.418 g) were heated together at 80° C. for 3 hours while stirring. After cooling, methanol (7.0 ml) and a 50% aqueous solution of sodium hydroxide (0.3 g) were added, and the mixture was allowed to stand at room temperature for 15 hours. The mixture was then adjusted to pH 6.0 with concentrated hydrochloric acid and concentrated to dryness under reduced pressure. The resulting residue was purified by silica gel column chromatography (carrier, 25 g; developing solvent, chloroform:methanol:water=65:25:1→65:25:4) to yield the desired compound (0.40 g).

IR (Nujol): ν 3370, 3160, 1580, 1565, 1425, 1380, 1320, 1115 cm$^{-1}$. NMR (90 MHz, CDCl$_3$—CD$_3$OD): δ0.87 (3H), 1.23–2.10 (38H), 2.23 (2H), 3.47 (2H), 3.60–3.90 (12H), 4.23 (2H), 4.43 (2H), 5.43 (1H), 6.97 (1H), 7.37 (1H), 7.60 (1H), 8.50 (2H), 9.63 (1H).

EXAMPLE 2

Production of
6-[3-[2-[2-[2-(2,2-dimethoxypropoxy)-3-octadecyloxy-propoxy]ethoxy]ethyl]imidazolio-1-yl]-hexanoate The procedure of Example 1 was applied to a reaction of the compound of Reference Example 11 (1.1 g) with methyl 6-bromohexanoate (0.836 g) to yield the desired compound (1.3 g).

IR (KBr): v 3430, 1560, 1405, 1375, 1250, 1165, 1110, 850 cm$^{-1}$. NMR (90 MHz, CDCl$_3$—CD$_3$OD): δ0.87 (3H), 1.10–1.73 (39H), 1.90 (2H), 2.20 (2H), 3.20 (6H), 3.30–3.67 (13H), 3.83 (2H), 4.23 (2H), 4.47 (2H), 7.43 (1H), 7.60 (1H), 9.43 (1H).

EXAMPLE 3

Production of 6-[3-[2-[2-8 3-octadecyloxy-2-(2-oxopropoxy)-propoxy]ethoxy]ethyl]imidazolio-1-yl]hexanoate The compound of Example 2 (1.3 g) was dissolved in a mixture of acetone (10.0 ml) and water (1.0 ml). To this solution, Amberlyst-15® (0.3 g) was added, followed by stirring at room temperature for 8 hours. After the Amberlyst-15® was removed by filtration, the filtrate was concentrated to dryness under reduced pressure. The resulting residue was purified by silica gel column chromatography (carrier, 20 g; developing solvent, chloroform:methanol=5:1→3:1, then chloroform:methanol:water=65:25:1→65:25:2) to yield the desired compound (0.68 g).

IR (Nujol): v 3420, 1730, 1715, 1560, 1110 cm$^{-1}$. NMR (90 MHz, CDCl$_3$—CD$_3$OD): δ0.87 (3H), 1.23–1.77 (36H), 1.77–2.00 (2H), 2.13 (3H), 3.33–3.70 (11H), 3.87 (2H), 4.27 (2H), 4.30 (2H), 4.50 (2H), 7.40 (1H), 7.60 (1H), 9.43 (1H).

EXAMPLE 4

Production of
6-[N,N-dimethyl-N-[2-[2-[2-[(2,2-dimethoxypropoxy)-3-octadecyloxypropoxy]ethoxy]ethyl]ammonio]-hexanoate The procedure of Example 1 was applied to a reaction of the compound of Reference Example 12 (0.85 g) with methyl 6-bromohexanoate (0.62 g) to yield the desired compound (0.47 g).

NMR(90 MHz, CDCl$_3$—D$_2$O): δ0.86 (3H), 1.00–2.00 (41H), 2.00–2.23 (2H), 3.33–4.00 (19H), 3.12 (6H), 3.18 (6H)

EXAMPLE 5

Production of
6-[N,N-dimethyl-N-[2-[2-[3-octadecyloxy-2-(2-oxopropoxy)propoxy]ethoxy]ethyl]ammonio]hexanoate The compound of Example 4 (250 mg) was subjected to the same reaction as that of Example 3 to yield the desired compound (86.4 mg).

IR (KBr): v 3425, 2920, 2850, 1730, 1560, 1460, 1400, 1120 cm$^{-1}$. NMR (90 MHz, CDCl$_3$): δ0.87 (3H), 1.05–1.90 (38H), 1.97–2.16 (5H), 2.90–4.03 (23H), 4.25 (2H).

EXAMPLE 6

Production of
2-[3-[2-[2-[2-hexyloxy-3-octadecyloxypropoxy]-ethoxy]ethyl]imidazolio-1-yl]acetate The procedure of Reference Example 4 was applied to a reaction of the compound of Reference Example 17 (0.714 g) with 1-ethoxycarbonylmethylimidazole (0.316 g) to yield 1-(1-ethoxycarbonylmethyl)-3-[2-[2-[2-hexyloxy-3-octadecyloxypropoxy]ethoxy]ethyl-]imidazolium chloride. The entire amount of this product was subjected to a hydrolysis reaction in the same way as Example 1 to yield the desired compound (0.57 g).

IR (Nujol): v 3380, 1625, 1450, 1375, 1110 cm$^{-1}$. NMR (90 MHz, CDCl$_3$—CD$_3$OD): δ0.87 (3H), 1.27 (40H), 3.27–3.63 (12H), 3.83 (2H), 4.37 (2H), 4.70 (2H), 7.33 (1H), 7.40 (1H), 9.07 (1H).

EXAMPLE 7

Production of
9-[3-[2-[2-[3-[3-octadecyloxy-2-(pyrimidin-2-yloxy)-propoxy]ethoxy]ethyl]imidazolio-1-yl]nonanoate The procedure of Example 1 was applied to a reaction of the compound of Reference Example 4 (1.0 g) with methyl 9-bromononanoate (0.49 g) to yield the desired compound (0.35 g).

IR (KBr): v 3420, 2925, 2860, 1577, 1560, 1464, 1423, 1325, 1310,1160, 1115 cm$^{-1}$. NMR (90 MHz, CDCl$_3$): δ0.86 (3H), 1.10–2.13 (44H), 2.31 (2H), 3.35–4.71 (16H), 5.46 (1H), 6.99 (1H), 7.50 (1H), 7.72 (1H), 8.53 (2H, d), 9.99 (1H).

EXAMPLE 8

Production of
4-[3-[2-[2-[3-octadecyloxy-2-(pyrimidin-2-yloxy)-propoxy]ethoxy]ethyl]imidazolio-1-yl]butyrate A mixture of the compound of Reference Example 4 (1.0 g), methyl γ-chlorobutyrate (0.73 g), and potassium iodide (0.09 g) was stirred at 80° C. for 1.5 hours, then 90° C. overnight, and then 120° C. for 2.5 hours. After cooling, methanol (12 ml) and a 50% aqueous solution of sodium hydroxide (1.14 g) were added, followed by stirring at room temperature for 2 hours. The mixture was then neutralized (pH 6.0) with 2N hydrochloric acid. The reaction mixture was concentrated to dryness and extracted with dichloromethane. The resulting extracts were combined and concentrated. The resulting residue was purified by silica gel column chromatography (carrier 40 g; developing solvent, chloroform:methanol:water=5:1:0→65:25:4) to yield the desired compound (0.62 g).

IR (KBr): v 3420, 2925, 2860, 1580, 1560, 1465, 1425, 1320, 1110 cm$^{-1}$. NMR (90 MHz, CDCl$_3$—CD$_3$OD): δ0.87 (3H), 1.06–1.82 (34H), 2.24 (2H), 3.33–3.95 (12H), 4.20–4.60 (4H), 5.45 (1H), 6.99 (1H), 7.51–7.68 (2H), 8.51 (2H), 9.39 (1H,s).

EXAMPLE 9

Production of
6-[N,N-dimethyl-N-[2-[2-[3-octadecyloxy-2-(pyrimidin-2-yloxy)propoxy]ethoxy]ethyl]ammonio]-hexanoate The procedure of Example 1 was applied to a reaction of the compound of Reference Example 13 (1.07 g) with methyl 6-bromohexanoate (0.84 g) to yield the desired compound (0.33 g).

IR (KBr): v 3400, 2930, 2860, 1630, 1575, 1560, 1540, 1463, 1455, 1425, 1330, 1110 cm$^{-1}$. NMR (90 MHz, CD$_3$OD): δ0.88 (3H), 1.17–2.00 (38H), 2.28 (2H), 3.13 (6H), 3.37–4.00 (16H), 5.46 (1H), 7.08 (1H), 8.58 (2H).

EXAMPLE 10

Production of 4-[4-[3-[2-[2-[3-octadecyloxy-2-(pyrimidin-2-yloxy)-propoxy]ethoxy]ethyl]imidazolio-1-yl]butyl]benzoate A mixture of the compound of Reference Example 4 (450 mg) and the compound of Reference Example 14 (591 mg) was heated at 110° C. for 2 hours while stirring. After cooling the reaction mixture, dichloromethane (1.0 ml) and trifluoroacetic acid (4.0 ml) were added, and the resulting mixture was allowed to stand at room temperature for 3 hours. The solvent was distilled off under reduced pressure. The resulting residue was neutralized with saturated aqueous sodium bicarbonate and then extracted with dichloromethane. After the extraction solvent was distilled off, the residue was purified by silica gel column chromatography (carrier, 15 g; developing solvent, chloroform:methanol:water=65:25:1→65:25:4) to yield the desired compound (450 mg).

IR (Nujol): v 3370, 1595, 1580, 1565, 1550, 1425, 1385, 1330, 1115 cm$^{-1}$. NMR (90 MHz, CDCl$_3$—CD$_3$OD): δ0.87 (3H), 1.20–1.90 (36H), 2.47 (2H), 3.43 (2H), 3.57–3.87 (8H), 4.07 (2H), 4.40 (2H), 5.43 (1H), 6.97 (3H), 7.27 (1H), 7.57 (1H), 7.87 (2H), 8.47 (2H), 9.53 (1H).

EXAMPLE 11

Production of 4-[4-[3-[2-[2-[3-octadecyloxy-2-(pyrimidin-2-yloxy)-propoxy]ethoxy]ethyl]imidazolio-1-yl]butyl]-cyclohexylcarboxylate The procedure of Example 10 was applied to a reaction of the compound of Reference Example 4 (780 mg) with the compound of Reference Example 15 (1.03 g) to yield the desired compound (690 mg).

IR (Nujol): v 3370, 1635, 1575, 1565, 1425, 1380, 1320, 1120 cm$^{-1}$. NMR (90 MHz, CDCl$_3$—CD$_3$OD): δ0.87 (3H), 1.10–2.40 (48H), 3.37–3.97 (12H), 4.23 (2H), 4.43 (2H), 5.47 (1H), 6.97 (1H), 7.43 (1H), 7.63 (1H), 8.50 (2H), 9.50 (1H).

EXAMPLE 12

Production of 3-[1-[2-[2-[3-octadecyloxy-2-(pyrimidin-2-yloxy)-propoxy]ethoxy]ethyl]pyridinio-3-yl]propionate The compound of Reference Example 3 (0.942 g) and ethyl pyridin-3-ylpropionate (0.448 g) were heated together at 110° C. for 1 hour while stirring. After cooling, the reaction mixture was dissolved in 70% hydrated methanol (15 ml). To this solution, triethylamine (1.0 g) was added, and the mixture was allowed to stand at room temperature for 60 hours. The solvent and the excess portion of the reagent were distilled off under reduced pressure. The resulting residue was purified by silica gel column chromatography (carrier, 30 g; developing solvent, chloroform:methanol:water=65:25:1→65:25:4) to yield the desired compound (0.58 g).

IR (Nujol): v 3400, 1575, 1560, 1420, 1320, 1115 cm$^{-1}$. NMR (90 MHz, CDCl$_3$—CD$_3$OD): δ0.87 (3H), 1.27 (32H), 2.57 (2H), 3.07 (2H), 3.37–3.80 (10H), 3.93 (2H), 4.73 (2H), 5.47 (1H), 6.97 (1H), 7.87 (1H), 8.30 (1H), 8.47 (2H), 8.67 (1H), 8.90 (1H).

EXAMPLE 13

Production of 3-[2-[2-[3-octadecyloxy-2-(pyrimidin-2-yloxy)-propoxy]ethoxy]ethyl]imidazolio-1-ylacetate The procedure of Example 6 was applied to a reaction of the compound of Reference Example 3 (707 mg) with ethyl 1-imidazolacetate (320 mg) to yield the desired compound (590 mg).

IR (Nujol): v 3400, 1640, 1620, 1575, 1565, 1425, 1380, 1365, 1310, 1115 cm$^{-1}$. NMR (90 MHz, CDCl$_3$—CD$_3$OD): δ0.87 (3H), 1.27 (32H), 3.43 (2H), 3.60–3.87 (10H), 4.33 (2H), 4.67 (2H), 5.43 (1H), 6.97 (1H), 7.33 (1H), 7.40 (1H), 8.50 (2H), 9.00 (1H).

EXAMPLE 14

Production of 1-(5-methoxycarbonylpentyl)-3-[2-[2-[3-octadecyloxy-2-(pyrimidin-2-yloxy)propoxy]ethoxy]-ethyl]imidazolium chloride.

The procedure of Reference Example 4 was applied to a reaction of the compound of Reference Example 3 (589 mg) with 1-(5-methoxycarbonylpentyl)imidazole (250 mg) to yield the desired compound (435 mg).

IR (Nujol): v 3380, 1730, 1570, 1560, 1420, 1320, 1160, 1105 cm$^{-1}$. NMR (90 MHz, CDCl$_3$—CD$_3$OD): δ0.87 (3H), 1.17–2.03 (38H), 2.37 (2H), 3.43 (2H), 3.60–3.93 (13H), 4.30 (2H), 4.53 (2H), 5.50 (1H), 7.00 (1H), 7.40 (1H), 7.73 (1H), 8.57 (2H), 9.80 (1H).

EXAMPLE 15

Production of 1-(3-ethoxycarbonyl-3-methyl)butyl-3-[2-[2-[3-octadecyloxy-2-(pyrimidin-2-yloxy)propoxy]-ethoxy]ethylimidazolium chloride The procedure of Reference Example 4 was applied to a reaction of the compound of Reference Example 3 (561 mg) with 1-(3-ethoxycarbonyl-3-methyl)-butylimidazole (500 mg) to yield the desired compound (135 mg).

IR (Nujol): v 3400, 1730, 1575, 1565, 1420, 1325, 1140, 1115 cm$^{-1}$. NMR (90 MHz, CDCl$_3$—CD$_3$OD): δ0.87 (3H), 1.17–1.70 (41H), 2.07–2.27 (2H), 3.43 (2H), 3.60–3.90 (10H), 4.13 (2H), 4.20–4.40 (2H), 4.60 (2H), 5.43 (1H), 6.93 (1H), 7.40 (1H), 7.73 (1H), 8.50 (2H), 10.50 (1H).

EXAMPLE 16

Production of 2,2-dimethyl-4-[3-[2-[2-[3-octadecyloxy-2-(pyrimidin-2-yloxy)propoxy]ethoxy]ethyl]imidazolio-1-yl]butyrate The compound of Example 15 (740 mg) was dissolved in methanol (30 ml). To this solution, an aqueous solution of 2N sodium hydroxide (20 ml) was added, and this mixture was stirred at 30° to 40° C. for 2.5 hours. After adding ammonium chloride (1.2 g), the resulting mixture was concentrated to dryness under reduced pressure. The resulting residue was eluted with chloroform, followed by distillation of the chloroform from the eluate layer. The resulting residue was purified by silica gel column chromatography (carrier, 20 g; developing solvent, chloroform:methanol=7:1→3:1) to yield the desired compound (300 mg).

IR (Nujol): v 3360, 1575, 1560, 1420, 1375, 1315, 1110 cm⁻¹. NMR (90 MHz, CDCl₃—CD₃OD): δ0.87 (3H), 1.20–1.67 (38H), 2.07 (2H), 3.47 (2H), 3.60–3.90 (10H), 4.20–4.53 (4H), 5.43 (1H), 6.97 (1H), 7.40 (1H), 7.60 (1H), 8.50 (2H), 9.40 (1H).

EXAMPLE 17

Production of 6-[1-[2-[2-[3-octadecyloxy-2-(pyrimidin-2-yloxy)-propoxy]ethoxy]ethyl]pyrrolidinio-1-yl]hexanoate The compound of Reference Example 3 (5.9 g) and pyrrolidine (7.1 g) were dissolved in toluene (30 ml), followed by stirring at room temperature for 40 hours. The reaction mixture was diluted with ether (150 ml) and washed with an aqueous solution of 0.01N sodium hydroxide (150 ml) and water (50 ml). The solvent was distilled off under reduced pressure to yield N-[2-[2-[3-octadecyloxy-2-(pyrimidin-2-yloxy)propoxy]ethoxy]e-thylpyrrolidine (5.65 g). To this compound (850 mg), ethyl 6-bromohexanoate (373 mg) and then potassium iodide (100 mg) were added, followed by stirring at 80° C. for 9 hours. Methanol (10 ml) and an aqueous solution of 2N sodium hydroxide (6 ml) were then added. After being allowed to stand at room temperature for 40 hours, the mixture was adjusted to pH 5 with 2N hydrochloric acid. The solvent was concentrated to dryness under reduced pressure. The resulting residue was purified by silica gel column chromatography (carrier, 20 g; developing solvent, chloroform:methanol:-water=65:25:4) to yield the desired compound (360 mg).

IR (Nujol): v 3380, 1575, 1560, 1420, 1375, 1320, 1110 cm⁻¹. NMR (90 MHz, CDCl₃—CD₃OD): δ0.87 (3H), 1.23–2.10 (38H), 2.10–2.40 (6H), 3.20–3.93 (20H), 5.47 (1H), 7.00 (1H), 8.53 (2H).

EXAMPLE 18

Production of 3-[3-[2-[2-[3-octadecyloxy-2-(pyrimidin-2-yloxy)-propoxy]ethoxy]ethyl]imidazolio-1-yl]propyl succinate 1-(3-Hydroxypropyl)-3-[2-[2-[3-octadecyloxy-2-(pyrimidin-2-yloxy)propoxy]ethoxy]ethyl]imidazolium chloride (655 mg), as obtained by reacting the compound of Reference Example 3 with 3-hydroxypropylimidazole in the same manner as in Reference Example 4, was dissolved in pyridine (2 ml). To this solution, succinic anhydride (600 mg) was added, followed by stirring at 45° C. for 3 hours. To the reaction mixture, water (0.4 ml) was added, followed by stirring under the same conditions as above for 15 minutes. The solvent was then distilled off under reduced pressure. The resulting residue was dissolved in a mixture of dichloromethane and ethanol (9:1, 60 ml) and washed with a mixture of saturated saline (40 ml) and saturated aqueous sodium bicarbonate (15 ml). The organic layer was collected and concentrated to dryness under reduced pressure. The resulting residue was purified by silica gel column chromatography (carrier, 20 g; developing solvent, chloroform:methanol:water=65:25:4) to yield the desired compound (390 mg).

IR (Nujol): v 3400, 1730, 1575, 1565, 1425, 1375, 1320, 1160, 1115 cm⁻¹. NMR (90 MHz, CDCl₃—CD₃OD): δ0.87 (3H), 1.27 (32H), 2.20 (2H), 2.53 (2H), 3.47 (2H), 3.60–3.87 (12H), 4.03 (2H), 4.40 (2H), 5.47 (1H), 6.97 (1H), 7.40 (1H), 7.60 (1H), 8.50 (2H), 9.60 (1H).

EXAMPLE 19

Production of 3-[1-[2-[2-[3-octadecyloxy-2-(pyrimidin-2-yloxy)-propoxy]ethoxy]ethyl]pyridinio-3-yl]propyl succinate 3-(3-Hydroxypropyl)-1-[2-[2-[3-octadecyloxy-2-(pyrimidin-2-yloxy)propoxy]ethoxy]ethyl]pyridinium chloride (524 mg), as obtained by reacting the compound of Reference Example 3 and 3-pyridinepropanol in the same manner as in Reference Example 4, was treated with succinic anhydride (600 mg) in the same manner as in Example 18 to yield the desired compound (480 mg).

IR (Nujol): v 1730, 1575, 1565, 1425, 1370, 1325, 1210, 1160, 1110 cm⁻¹. NMR (90 MHz, CDCl₃—CD₃OD): δ0.87 (3H), 1.23 (32H), 2.07 (2H), 2.60 (4H), 3.00 (2H), 3.47 (2H), 3.60–3.77 (8H), 3.96 (2H), 4.10 (2H), 4.93 (2H), 5.43 (1H), 6.97 (1H), 8.00 (1H), 8.27 (1H), 8.50 (2H), 8.90 (1H), 9.07 (1H).

EXAMPLE 20

Production of 6-[3-[2-[2-[2-[3-octadecyloxy-2-(pyrimidin-2-yloxy)-propoxy]ethoxy]ethoxy]ethyl]imidazolio-1-yl]-hexanoate The procedure of Example 6 was applied to a reaction of the compound of Reference Example 18 (847 mg) with methyl 6-(imidazol-1-yl)hexanoate (400 mg) to yield the desired compound (670 mg).

IR (Nujol): v 3370, 1570, 1560, 1420, 1375, 1315, 1110 cm⁻¹. NMR (90 MHz, CDCl₃—CD₃OD): δ0.87 (3H), 1.23–2.07 (38H), 2.20 (2H), 3.37–4.03 (16H), 4.23 (2H), 4.47 (2H), 5.43 (1H), 6.97 (1H), 7.43 (1H), 7.60 (1H), 8.50 (2H), 9.47 (1H).

EXAMPLE 21

Production of 4-[3-[2-[2-[2-[3-octadecyloxy-2-(pyrimidin-2-yloxy)-propoxy]ethoxy]ethoxy]ethyl]imidazolio-1-yl]-butyrate The procedure of Example 6 was applied to a reaction of the compound of Reference Example 18 (800 mg) with ethyl 4-(imidazol-1-yl)butyrate (600 mg) to yield the desired compound (480 mg).

IR (Nujol): v 3390, 1575, 1560, 1420, 1375, 1315, 1110, 1105 cm⁻¹. NMR (90 MHz, CDCl₃—CD₃OD): δ0.87 (3H), 1.23–2.07 (32H), 2.10–2.23 (4H), 3.33–3.90 (16H), 4.27 (2H), 4.40 (2H), 5.43 (1H), 6.93 (1H), 7.47 (1H), 7.53 (1H), 8.50 (2H), 9.23 (1H).

EXAMPLE 22

Production of 3-[1-[4-[3-octadecyloxy-2-(pyrimidin-2-yloxy)-propoxy]butyl]pyridinio-3-yl]propionate The procedure of Example 6 was applied to a reaction of the compound of Reference Example 19 (1.03 g) with ethyl 3-(pyridin-3-yl)propionate (450 mg) to yield the desired compound (720 mg).

IR (Nujol): v 3350, 1625, 1560, 1420, 1320, 1110 cm⁻¹. NMR (90 MHz, CDCl₃—CD₃OD): δ0.87 (3H), 1.27 (32H), 1.60 (2H), 2.07 (2H), 2.57 (2H), 3.07 (2H), 3.37–3.77 (8H), 4.67 (2H), 5.47 (1H), 6.97 (1H), 7.90 (1H), 8.37 (1H), 8.50 (2H), 8.77 (1H), 8.93 (1H).

EXAMPLE 23

Production of 5-[1-[4-[3-octadecyloxy-2-(pyrimidin-2-yloxy)-propoxy]butyl]pyridinio-3-yl]pentanoate The procedure of Example 6 was applied to a reaction of the compound of Reference Example 19 (865 mg) with ethyl 5-(pyridin-3-yl)valerate (414 mg) to yield the desired compound (250 mg).

IR (Nujol): ν 3420, 1630, 1580, 1565, 1425, 1320, 1210, 1185, 1115, 1040 cm$^{-1}$. NMR (90 MHz, CDCl$_3$—CD$_3$OD): δ0.87 (3H), 1.27 (32H), 1.40–1.83 (6H), 1.93–2.27 (4H), 2.87 (2H), 3.07 (2H), 3.33–3.77 (8H), 4.67 (2H), 5.43 (1H), 6.97 (1H), 7.93 (1H), 8.27 (1H), 8.50 (2H), 8.80 (1H), 9.03 (1H).

EXAMPLE 24

Production of 4-[3-[2-[2-[3-(12-cyclohexyldodecyloxy)-2-(pyrimidin-2-yloxy)propoxy]ethoxy]ethyl]imidazolio-1-yl]butyrate The procedure of Example 6 was applied to a reaction of the compound of Reference Example 21 (0.70 g) with ethyl 4-(imidazol-1-yl)butyrate (0.60 g) to yield the desired compound (0.51 g).

IR (Neat): ν 3400, 3050, 2930, 2850, 1570, 1465, 1445, 1420, 1320, 1120, 810 cm$^{-1}$. NMR (90 MHz, CDCl$_3$): δ1.00–1.77 (33H), 2.00–2.30 (4H), 3.40–3.90 (12H), 4.27–4.60 (4H), 5.45 (1H), 6.95 (1H), 7.48 (1H), 7.60 (1H), 8.50 (2H), 9.92 (1H).

EXAMPLE 25

Production of 6-[3-[2-[2-[3-(12-cyclohexyldodecyloxy)-2-(pyrimidin-2-yloxy)propoxy]ethoxy]ethyl]imidazolio-1-yl]hexanoate The procedure of Example 6 was applied to a reaction of the compound of Reference Example 21 (0.70 g) with ethyl 6-(imidazol-1-yl)hexanoate (0.60 g) to yield the desired compound (0.53 g).

IR (Neat): ν 3390, 3050, 2930, 2860, 1580, 1560, 1450, 1420, 1320, 1120, 805 cm$^{-1}$. NMR (90 MHz, CDCl$_3$): δ1.00–2.00 (39H), 2.22 (2H), 3.33–3.90 (12H), 4.27 (2H), 4.55 (2H), 5.45 (1H), 6.97 (1H), 7.41 (1H), 7.65 (1H), 8.52 (2H), 10.70 (1H).

EXAMPLE 26

Production of 3-[3-[3-octadecyloxy-2-(pyrimidin-2-yloxy)]-propoxy]-propyl]pyridinio-1-ylacetate The compound of Reference Example 23 (1.59 g) and ethyl bromoacetate (3.25 ml) were dissolved in isopropyl ether (17 ml), followed by stirring at 45° C. overnight. The solvent and the excess portion of the ethyl bromoacetate were distilled off under reduced pressure. The resulting residue was dissolved in methanol (60 ml). To this solution, 0.2N sodium hydroxide (32 ml) was added, followed by stirring at room temperature for 1 hour. After neutralization of the mixture with 2N hydrochloric acid, the solvent was distilled off. The resulting residue was purified by silica gel column chromatography (carrier, 100 g; developing solvent, chloroform:methanol:water=65:25:4) to yield the desired compound (430 mg).

IR (Neat): ν 3425, 2920, 2850, 1665, 1640, 1575, 1560, 1465, 1422, 1370, 1320, 1120, 715, 708 cm$^{-1}$. NMR (90 MHz, CDCl$_3$): δ0.86 (3H), 1.26 (32H), 1.75–2.18 (2H), 2.65–3.06 (2H), 3.20–3.90 (8H), 5.44 (1H), 5.70 (2H), 6.96 (1H), 7.75–8.06 (1H), 8.06–8.33 (1H), 8.53 (2H), 9.10–9.45 (2H).

What is claimed is:

1. A compound of the formula:

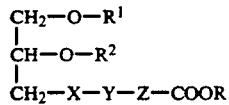

wherein

R represents a hydrogen atom or an alkyl group having 1 to 6 carbon atoms;

R$^1$ represents an alkyl group having 8 to 20 carbon atoms which may be substituted by phenyl, naphthyl, C$_3$–C$_8$ cycloalkyl, C$_1$–C$_6$ alkyl, vinyl, ethynyl, hydroxy, C$_1$–C$_6$ alkoxy, halogen or oxo;

R$^2$ represents a hydrogen atom, an alkyl group having 1 to 6 carbon atoms, an alkanoyl group having 1 to 6 carbon atoms or a nitrogen-containing 5- to 7-membered heterocyclic group selected from the class consisting of pyrrolyl, imidazolyl, pyrazolyl, oxazolyl, isooxazolyl, thiazolyl, 1,2,3-oxadiazolyl, triazolyl, tetrazolyl, thiadiazolyl, piperidinyl, N-methylpiperazinyl, N-ethylpiperazinyl, morpholinyl, thiomorpholinyl, pyridyl, pyridazinyl, pyrimidinyl, pyrazinyl, triazinyl, azepinyl, diazepinyl, benzoxazolyl, benzothiazolyl, isoindolyl, indolyl, indolidinyl, indazolyl, purinyl, quinolyl, isoquinolyl, quinolizinyl, phthalazinyl, quinoxalinyl, quinazolinyl, cinnolinyl and pteridinyl, each of said alkyl group, alkanoyl group and nitrogen-containing 5- to 7-membered heterocyclic group being unsubstituted or substituted by halogen, C$_1$–C$_6$ alkyl, C$_2$–C$_6$alkenyl, C$_3$–C$_6$ cycloalkyl, C$_5$–C$_6$ cycloalkenyl, phenyl-C$_1$–C$_6$ alkyl, phenyl, C$_1$–C$_6$ alkylthio, C$_1$–C$_6$ alkylsulfinyl, phenylsulfinyl, C$_1$–C$_6$ alkylsulfonyl, phenylsulfonyl, mercapto, sulfino, sulfo, phosphono, sulfamoyl, N—C$_1$–C$_6$ alkylsulfamoyl, N,N—di—C$_1$–C$_6$ alkylsulfamoyl, 3- to 6-membered cyclic aminosulfonyl selected from the class consisting of 1-pyrrolidinylsulfonyl, 1-piperidinylsulfonyl, 1-piperazinylsulfonyl, 4-methylpiperazin-1-ylsulfonyl and morpholinylsulfonyl, imino, amidino, amino, N—C$_1$–C$_6$ alkylamino, N,N—di—C$_1$–C$_6$ alkylamino, 3- to 6-membered cyclic amino selected from the class consisting of 1-azetidinyl, 1-pyrrolidinyl, 1-piperidinyl, 1-piperazinyl, 4-methylpiperazin-1-yl and morpholino, C$_1$–C$_6$ alkanoyl, C$_1$–C$_6$ alkanoylamino, benzamido, benzoyl, C$_1$–C$_6$ alkanoyloxy, benzoyloxy, C$_1$–C$_6$ alkoxy, C$_2$–C$_7$ alkoxycarbonyl, phenoxy, phenylthio, hydroxy, oxo, thioxo, epoxy, hydroxy-C$_1$–C$_6$ alkyl, amino-C$_1$–C$_6$ alkyl, carboxy, carbamoyl, N—C$_1$–C$_6$ alkylcarbamoyl, N,N—di—C$_1$–C$_6$ alkylcarbamoyl, 3- to 6-membered cyclic aminocarbonyl selected from the class consisting of 1-azetidinylcarbonyl, 1-pyrrolidinylcarbonyl, 1-piperidinylcarbonyl, 1-piperazinylcarbonyl, 4-methylpiperazin-1-ylcarbonyl and morpholinocarbonyl, cyano, trifluoro or ureido;

X represents a divalent group of the formula: —(OCH$_2$CH$_2$)p— wherein p represents an integer of 1 to 5, a divalent group of the formula: —O(CH$_2$)q— wherein q represents an integer of 3 to 8, or a divalent group of the formula: —(OCH$_2$CH$_2$)p—J—(CH$_2$)q— wherein J represents an oxygen atom or a group of the formula: —S(O)r— wherein r represents an integer of 0 to 2, and p and q are as defined as above;

Y represents (i) a divalent group containing a tertiary nitrogen atom of the formula:

wherein $R^3$ represents an alkyl group having 1 to 6 carbon atoms, (ii) a divalent heterocyclic group containing tertiary nitrogen atom(s) selected from the class consisting of pyrrolidine-1, (2 or 3)-diyl, pyrroline-1, (2 or 3)-diyl, pyrrole-1, (2 or 3)-diyl, imidazoline-1, (2, 4 or 5)-diyl, imidazole-1, (2, 4 or 5)-diyl, pyrazoline-1, (3, 4 or 5)-diyl, pyrazole-1, (3, 4 or 5)-diyl, oxazole-(2, 4 or 5)-diyl, thiazole-(2, 4 or 5)diyl, piperidine-1, (2, 3 or 4)-diyl, pyridine-(2, 3, 4 or 5)-diyl, pyrimidine-(2, 4, 5 or 6)-diyl, pyridazine-(3, 4, 5 or 6)-diyl, pyrazine-(2, 3, 5 or 6)-diyl, piperazine-1, (2 or 3)-diyl, morpholine-(2 or 3), 4-diyl, thiomorpholine-(2 or 3), 4-diyl, benzoxazole-(2, 4, 5, 6 or 7)-diyl, benzothiazole-(2, 4, 5, 6 or 7)-diyl, isoindole-2, (1, 3, 4, 5, 6 or 7)-diyl, indole-1, (2, 3, 4, 5, 6 or 7)-diyl, purinediyl, isoquinolinediyl, quinolinediyl, phthalazinediyl, quinoxalinediyl, quinazolinediyl, cinnolinediyl and pteridinediyl, (iii) a divalent group containing a quaternary nitrogen atom of the formula:

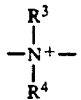

wherein $R^3$ and $R^4$ independently represents an alkyl group having 1 to 6 carbon atoms, or $R^3$ and $R^4$ may, together with the adjacent nitrogen atom, form a cyclic ammonium group selected from the class consisting of pyrrolinio-1,1-diyl, pyrrolidinio-1,1-diyl, imidazolio-1,1-diyl, imidazolinio-1,1-diyl, pyrazolio-(1,1) or (2,2)-diyl, piperidinio-1,1-diyl, piperazinio-1,1-diyl, morpholinio-4,4-diyl, thiomorpholinio-4,4-diyl, indolinio-1,1-diyl and isoindolinio-2,2-diyl, or (iv) a divalent heterocyclic group containing quaternary nitrogen atom(s) selected from the class consisting of 1-($C_1$-$C_6$ alkyl)-pyrrolidinio-1, (2 or 3)-diyl, 1-($C_1$-$C_6$ alkyl)pyrrolinio-1, (2 or 3)-diyl, imidazolio-1,3-diyl, (1 or 3)-mono ($C_1$-$C_6$ alkyl)imidazolio-(3 or 1), (2 or 4)-diyl, imidazolinio-1,3-diyl, (1 or 3)-mono ($C_1$-$C_6$ alkyl)imidazolinio-(3 or 1), (2 or 4)-diyl, oxazolio-3, (2, 4 or 5)-diyl, thiazolio-3, (2, 4 or 5)-diyl, pyridinio-1, (2, 3 or 4)-diyl, 1-($C_1$-$C_6$ alkyl)piperidinio-1, (2, 3 or 4)-diyl, 1-($C_1$-$C_6$ alkyl)piperazinio-1, (2 or 3)-diyl, pyrazinio-1, (2 or 3)-diyl, pyrimidinio-1, (2, 4, 5 or 6)-diyl, pyridazinio-1, (3 or 4)-diyl, 4-($C_1$-$C_6$ alkyl)morpholinio-4, (2 or 3)-diyl, 4-($C_1$-$C_6$ alkyl)thiomorpholinio-4, (2 or 3)-diyl, benzoxazolio-1, (2, 4, 5, 6 or 7)-diyl, benzothiazolio-1, (2, 4, 5, 6 or 7)-diyl, quinolinio-1, (2, 3, 4, 5, 6, 7 or 8)-diyl, isoquinolinio-2, (1, 3, 4, 5, 6, 7 or 8)-diyl and (1,1 or 1,4)-di ($C_1$-$C_6$ alkyl)piperazinio-(4 or 1), (2 or 3)-diyl, each of said alkyl groups represented by $R^3$ and $R^4$, divalent heterocyclic group containing tertiary nitrogen atom(s), cyclic ammonium group and divalent heterocyclic group containing quaternary nitrogen atom(s) being unsubstituted or substituted by halogen, $C_1$-$C_6$ alkyl, $C_2$-$C_6$ alkenyl, $C_3$-$C_6$ cycloalkyl, $C_5$-$C_6$ cycloalkenyl, phenyl-$C_1$-$C_6$ alkyl, phenyl, $C_1$-$C_6$ alkylthio, $C_1$-$C_6$ alkylsulfinyl, phenylsulfinyl, $C_1$-$C_6$ alkylsulfonyl, phenylsulfonyl, mercapto, sulfino, sulfo, phosphono, sulfamoyl, N—$C_1$-$C_6$ alkylsulfamoyl, N,N—di—$C_1$-$C_6$ alkylsulfamoyl, 3- to 6-membered cyclic aminosulfonyl selected from the class consisting of 1-pyrrolidinylsulfonyl, 1-piperidinylsulfonyl, 1-piperazinylsulfonyl, 4-methylpiperazin-1-ylsulfonyl and morpholinylsulfonyl, imino, amidino, amino, N—$C_1$-$C_6$ alkylamino, N,N—di—$C_1$-$C_6$ alkylamino, 3- to 6-membered cyclic amino selected from the class consisting of 1-azetidinyl, 1-pyrrolidinyl, 1-piperidinyl, 1-piperazinyl, 4-methylpiperazin-1-yl and morpholino, $C_1$-$C_6$ alkanoyl, $C_1$-$C_6$ alkanoylamino, benzamido, benzoyl, $C_1$-$C_6$ alkanoyloxy, benzoyloxy, $C_1$-$C_6$ alkoxy, $C_2$-$C_7$ alkoxycarbonyl, phenoxy, phenylthio, hydroxy, oxo, thioxo, epoxy, hydroxy-$C_1$-$C_6$ alkyl, amino-$C_1$-$C_6$ alkyl, carboxy, carbamoyl, N—$C_1$-$C_6$ alkylcarbamoyl, N,N—di—$C_1$-$C_6$ alkylcarbamoyl, 3-to 6-membered cyclic aminocarbonyl selected from the class consisting of 1-azetidinylcarbonyl, 1-pyrrolidinylcarbonyl, 1-piperidinylcarbonyl, 1-piperazinylcarbonyl, 4-methylpiperazin-1-ylcarbonyl and morpholinocarbonyl, cyano, trifluoro or ureido;

Z represents (i) an alkylene group having 1 to 13 carbon atoms, (ii) a group of the formula: —Q—T—W— wherein Q and W independently represent an alkylene group having 1 to 12 carbon atoms, the total number of carbon atoms contained in Q and W being an integer of 2 to 13, and T represents a phenylene group, a naphthylene group, a 3- to 8-membered cycloalkylene group, —CH=CH—, —C≡C—, —NH—, —NH—C(=O)—, —C(=O)—NH—, —O—, —O—C(=O)—, —C(=O)—O—, —S—, —SO— or $SO_2$—, or (iii) a group of the formula: —Q—T— or —T—W— wherein Q and W represent an alkylene group having 1 to 13 carbon atoms and T represents a phenylene group, a naphthylene group, a 3- to 8-membered cycloalkylene group, —CH=CH— or —C≡C—, each of said alkylene groups in above (i), (ii) and (iii) being unsubstituted or substituted by halogen, $C_1$-$C_6$ alkyl, $C_2$-$C_6$ alkenyl, $C_3$-$C_6$ cycloalkyl, $C_5$-$C_6$ cycloalkenyl, phenyl-$C_1$-$C_6$ alkyl, phenyl, $C_1$-$C_6$ alkylthio, $C_1$-$C_6$ alkylsulfinyl, phenylsulfinyl, $C_1$-$C_6$ alkylsulfonyl, phenylsulfonyl, mercapto, sulfino, sulfo, phosphono, sulfamoyl, N—$C_1$-$C_6$ alkylsulfamoyl, N,N—di—$C_1$-$C_6$ alkylsulfamoyl, 3- to 6-membered cyclic aminosulfonyl selected from the class consisting of 1-pyrrolidinylsulfonyl, 1-piperidinylsulfonyl, 1-piperazinylsulfonyl, 4-methylpiperazin-1-ylsulfonyl and morpholinylsulfonyl, imino, amidino, amino, N—$C_1$-$C_6$ alkylamino, N,N—di—$C_1$-$C_6$ alkylamino, 3- to 6-membered cyclic amino selected from the class consisting of 1-azetidinyl, 1-pyrrolidinyl, 1-piperidinyl, 1-piperazinyl, 4-methylpiperazin-1-yl and morpholino, $C_1$-$C_6$ alkanoyl, $C_1$-$C_6$ alkanoylamino, benzamido, benzoyl, $C_1$-$C_6$ alkanoyloxy, benzoyloxy, $C_1$-$C_6$ alkoxy, $C_2$-$C_7$ alkoxycarbonyl, phenoxy, phenylthio, hydroxy, oxo, thioxo, epoxy, hydroxy- C₁–C₆ alkyl, amino-C₁–C₆ alkyl, carboxy, carbamoyl, N—C₁–C₆ alkylcarbamoyl, N,N—di—C₁–C₆ alkylcarbamoyl, 3- to 6-membered cyclic aminocarbonyl selected from the class consisting of 1-azetidinylcarbonyl, 1-pyrrolidinylcarbonyl, 1-piperidinylcarbonyl, 1-piperazinylcarbonyl, 4-methylpiperazin-1-ylcarbonyl and morpholinocarbonyl, cyano, trifluoro or ureido; or a pharmaceutically acceptable salt thereof, provided that when R² represents a hydrogen atom, an alkyl group or an alkanoyl group which is unsubstituted or substituted according to the above definition, Y represents a divalent heterocyclic group containing tertiary nitrogen atom(s) selected from the class consisting of pyrrolidine-1, (2 or 3)-diyl, pyrroline-1, (2 or 3)-diyl, pyrrole-1, (2 or 3)-diyl, imidazoline-1, (2, 4 or 5)-diyl, imidazole-1, (2, 4 or 5)-diyl, pyrazoline-1, (3, 4 or 5)-diyl, pyrazole-1, (3, 4 or 5)-diyl, oxazole-(2, 4 or 5)-diyl, thiazole-(2, 4 or 5)diyl, piperidine-1, (2, 3 or 4)-diyl, pyridine-(2, 3, 4 or 5)-diyl, pyrimidine-(2, 4, 5 or 6)-diyl, pyridazine-(3, 4, 5 or 6)-diyl, pyrazine-(2, 3, 5 or 6)-diyl, piperazine-1, (2 or 3)-diyl, morpholine-(2 or 3), 4-diyl, thiomorpholine-(2 or 3), 4-diyl, benzoxazole-(2, 4, 5, 6 or 7)-diyl, benzothiazole-(2, 4, 5, 6 or 7)-diyl, isoindole-2, (1, 3, 4, 5, 6 or 7)-diyl, indole-1, (2, 3, 4, 5, 6 or 7)-diyl, purinediyl, isoquinolinediyl, quinolinediyl, phthalazinediyl, quinoxalinediyl, quinazolinediyl, cinnolinediyl and pteridinediyl, a divalent group containing a quaternary nitrogen atom of the formula:

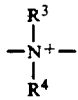

wherein R³ and R⁴, together with the adjacent nitrogen atom, form a cyclic ammonium group selected from the class consisting of pyrrolinio-1,1-diyl, pyrrolidinio-1,1-diyl, imidazolio-1,1-diyl, imidazolinio-1,1-diyl, pyrazolio-(1,1) or (2,2)-diyl, piperidinio-1,1-diyl, piperazinio-1,1-diyl, morpholinio-4,4-diyl, thiomorpholinio-4,4-diyl, indolinio-1,1-diyl and isoindolinio-2,2-diyl, or a divalent heterocyclic group containing quaternary nitrogen atom(s) selected from the class consisting of 1-(C₁–C₆ alkyl)pyrrolidinio-1, (2 or 3)-diyl, 1-(C₁–C₆ alkyl)pyrrolinio-1, (2 or 3)-diyl, imidazolio-1,3-diyl, (1 or 3)-mono (C₁–C₆ alkyl)imidazolio-(3 or 1), (2 or 4)-diyl, imidazolinio-1,3-diyl, (1 or 3)-mono (C₁–C₆ alkyl)imidazolinio-(3 or 1), (2 or 4)-diyl, oxazolio-3, (2, 4 or 5)-diyl, thiazolio-3, (2, 4 or 5)-diyl, pyridinio-1, (2, 3 or 4)-diyl, 1-(C₁–C₆ alkyl)piperidinio-1, (2, 3 or 4)-diyl, 1-(C₁–C₆ alkyl)piperazinio-1, (2 or 3)-diyl, pyrazinio-1, (2 or 3)-diyl, pyrimidinio-1, (2, 4, 5 or 6)-diyl, pyridazinio-1, (3 or 4)-diyl, 4-(C₁–C₆ alkyl)morpholinio-4, (2 or 3)-diyl, 4-(C₁–C₆ alkyl)thiomorpholinio-4, (2 or 3)-diyl, benzoxazolio-1, (2, 4, 5, 6 or 7)-diyl, benzothiazolio-1, (2, 4, 5, 6 or 7)-diyl, quinolinio-1, (2, 3, 4, 5, 6, 7 or 8)-diyl, isoquinolinio-2, (1, 3, 4, 5, 6, 7 or 8)-diyl and (1,1 or 1,4)-di(C₁–C₆ alkyl)piperazinio-(4 or 1), (2 or 3)-diyl, each of said heterocyclic group containing tertiary nitrogen atom(s), cyclic ammonium group and divalent heterocyclic group containing quaternary nitrogen atom(s) being unsubstituted or substituted by halogen, C₁–C₆ alkyl, C₂–C₆ alkenyl, C₃–C₆ cycloalkyl, C₅–C₆ cycloalkenyl, phenyl-C₁–C₆ alkyl, phenyl, C₁–C₆ alkylthio, C₁–C₆ alkylsulfinyl, phenylsulfinyl, C₁–C₆ alkylsulfonyl, phenylsulfonyl, mercapto, sulfino, sulfo, phosphono, sulfamoyl, N—C₁–C₆ alkylsulfamoyl, N,N—di—C₁–C₆ alkylsulfamoyl, 3- to 6-membered cyclic aminosulfonyl selected from the class consisting of 1-pyrrolidinylsulfonyl, 1-piperidinylsulfonyl, 1-piperazinylsulfonyl, 4-methylpiperazin-1-ylsulfonyl and morpholinylsulfonyl, imino, amidino, amino, N—C₁–C₆ alkylamino, N,N—di—C₁–C₆ alkylamino, 3- to 6-membered cyclic amino selected from the class consisting of 1-azetidinyl, 1-pyrrolidinyl, 1-piperidinyl, 1-piperazinyl, 4-methylpiperazin-1-yl and morpholino, C₁–C₆ alkanoyl, C₁–C₆ alkanoylamino, benzamido, benzoyl, C₁–C₆ alkanoyloxy, benzoyloxy, C₁–C₆ alkoxy, C₂–C₇ alkoxycarbonyl, phenoxy, phenylthio, hydroxy, oxo, thioxo, epoxy, hydroxy-C₁–C₆ alkyl, amino-C₁–C₆ alkyl, carboxy, carbamoyl, N—C₁–C₆ alkylcarbamoyl, N,N—di—C₁–C₆ alkylcarbamoyl, 3- to 6-membered cyclic aminocarbonyl selected from the class consisting of 1-azetidinylcarbonyl, 1-pyrrolidinylcarbonyl, 1-piperidinylcarbonyl, 1-piperazinylcarbonyl, 4-methylpiperazin-1-ylcarbonyl and morpholinocarbonyl, cyano, trifluoro or ureido.

2. A compound according to claim 1 or a salt thereof, wherein R represents a hydrogen atom.

3. A compound according to claim 1 or a salt thereof, wherein R¹ represents an alkyl group having 8 to 20 carbon atoms which may be substituted by C₃–C₈ cycloalkyl.

4. A compound according to claim 1 or a salt thereof, wherein R² represents a nitrogen-containing 5- to 7-membered heterocyclic group selected from the class consisting of pyrrolyl, imidazolyl, pyrazolyl, oxazolyl, isooxazolyl, thiazolyl, 1,2,3-oxadiazolyl, triazolyl, tetrazolyl, thiadiazolyl, piperidinyl, N-methylpiperazinyl, N-ethylpiperazinyl, morpholinyl, thiomorpholinyl, pyridyl, pyridazinyl, pyrimidinyl, pyrazinyl, triazinyl, azepinyl, diazepinyl, benzoxazolyl, benzothiazolyl, isoindolyl, indolyl, indolidinyl, indazolyl, purinyl, quinolyl, isoquinolyl, quinolizinyl, phthalazinyl, quinoxalinyl, quinazolinyl, cinnolinyl and pteridinyl.

5. A compound according to claim 4 or a salt thereof, wherein R² represents a pyrimidinyl group.

6. A compound according to claim 1 or a salt thereof, wherein X represents a group of the formula:

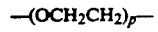

wherein p represents 2 or 3.

7. A compound according to claim 1 or a salt thereof, wherein Y represents a divalent heterocyclic group containing quaternary nitrogen atom(s) selected from the class consisting of 1-(C₁–C₆ alkyl)pyrrolidinio-1, (2 or 3)-diyl, 1-(C₁–C₆ alkyl)pyrrolinio-1, (2 or 3)-diyl, imidazolio-1,3-diyl, (1 or 3)-mono (C₁–C₆ alkyl)imidazolio-(3 or 1), (2 or 4)-diyl, imidazolinio-1,3-diyl, (1 or 3)-mono (C₁–C₆ alkyl)imidazolinio-(3 or 1), (2 or 4)-diyl, oxazolio-3, (2, 4 or 5)-diyl, thiazolio-3, (2, 4 or 5)-diyl, pyridinio-1, (2, 3 or 4)-diyl, 1-(C₁–C₆ alkyl)piperidinio-1, (2, 3 or 4)-diyl, 1-(C₁–C₆ alkyl)piperazinio-1, (2 or 3)-diyl, pyrazinio-1, (2 or 3)-diyl, pyrimidinio-1, (2, 4, 5 or 6)-diyl, pyridazinio-1, (3 or 4)-diyl, 4-($C_1$-$C_6$ alkyl)morpholinio-4, (2 or 3)-diyl, 4-($C_1$-$C_6$ alkyl)thiomorpholinio-4, (2 or 3)-diyl, benzoxazolio-1, (2, 4, 5, 6 or 7)-diyl, benzothiazolio-1, (2, 4, 5, 6 or 7)-diyl, quinolinio-1, (2, 3, 4, 5, 6, 7 or 8)-diyl, isoquinolinio-2, (1, 3, 4, 5, 6, 7 or 8)-diyl and (1,1 or 1,4)-di($C_1$-$C_6$ alkyl)piperazinio-(4 or 1), (2 or 3)-diyl.

8. A compound according to claim 7 or a salt thereof, wherein Y represents imidazolio-1,3-diyl or pyridinio-1,3-diyl.

9. A compound according to claim 1 or a salt thereof, wherein Z represents an alkylene group having 1 to 13 carbon atoms.

10. An intramolecular salt according to claim 1, which is represented by the formula:

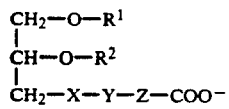

wherein $R^1$ represents an alkyl group having 8 to 20 carbon atoms which may be substituted by $C_3$-$C_8$ cycloalkyl;

$R^2$ represents a nitrogen-containing 5- to 7-membered heterocyclic group selected from the class consisting of pyrrolyl, imidazolyl, pyrazolyl, oxazolyl, isooxazolyl, thiazolyl, 1,2,3-oxadiazolyl, triazolyl, tetrazolyl, thiadiazolyl, piperidinyl, N-methylpiperazinyl, N-ethylpiperazinyl, morpholinyl, thiomorpholinyl, pyridyl, pyridazinyl, pyrimidinyl, pyrazinyl, triazinyl, azepinyl, diazepinyl, benzoxazolyl, benzothiazolyl, isoindolyl, indolyl, indolidinyl, indazolyl, purinyl, quinolyl, isoquinolyl, quinolizinyl, phthalazinyl, quinoxalinyl, quinazolinyl, cinnolinyl and pteridinyl;

X represents a divalent group of the formula: —(OCH$_2$CH$_2$)p— wherein p represents 2 or 3;

Y represents a divalent heterocyclic group containing a quaternary nitrogen atom selected from the class consisting of 1-($C_1$-$C_6$ alkyl)pyrrolidinio-1, (2 or 3)-diyl, 1-($C_1$-$C_6$ alkyl)pyrrolinio-1, (2 or 3)-diyl, imidazolio-1,3-diyl, (1 or 3)-mono ($C_1$-$C_6$ alkyl)imidazolio-(3 or 1), (2 or 4)-diyl, imidazolinio-1,3-diyl, (1 or 3)-mono ($C_1$-$C_6$ alkyl)imidazolinio-(3 or 1), (2 or 4)-diyl, oxazolio-3, (2, 4 or 5)-diyl, thiazolio-3, (2, 4 or 5)-diyl, pyridinio-1, (2, 3 or 4)-diyl, 1-($C_1$-$C_6$ alkyl)piperidinio-1, (2, 3 or 4)-diyl, 1-($C_1$-$C_6$ alkyl)piperazinio-1, (2 or 3)-diyl, pyrazinio-1, (2 or 3)-diyl, pyrimidinio-1, (2, 4, 5 or 6)-diyl, pyridazinio-1(3 or 4)-diyl, 4-($C_1$-$C_6$ alkyl)morpholinio-4, (2 or 3)-diyl, 4-($C_1$-$C_6$ alkyl)thiomorpholinio-4, (2 or 3)-diyl, benzoxazolio-1, (2, 4, 5, 6 or 7)-diyl, benzothiazolio-1, (2, 4, 5, 6 or 7)-diyl, quinolinio-1, (2, 3, 4, 5, 6, 7 or 8)-diyl, isoquinolinio-2, (1, 3, 4, 5, 6, 7 or 8)-diyl and (1, 1 or 1,4)-di ($C_1$-$C_6$ alkyl)piperazinio-(4 or 1), (2 or 3)-diyl; and Z represents an alkylene group having 1 to 13 carbon atoms.

11. An intramolecular salt according to claim 10, which is 6-[3-[2-[2-[3-octadecyloxy-2-(pyrimidin-2-yloxy)-propoxy]ethoxy]ethyl]imidazolio-1-yl]hexanoate.

12. An intramolecular salt according to claim 10, which is 4-[3-[2-[2-[3-octadecyloxy-2-(pyrimidin-2-yloxy)-propoxy]ethoxy]ethyl]imidazolio-1-yl]butyrate.

13. An intramolecular salt according to claim 10, which is 3-[1-[2-[2-[3-octadecyloxy-2-(pyrimidin-2-yloxy)-propoxy]ethoxy]ethyl]pyridinio-3-yl]propionate.

* * * * *